(12) United States Patent
Stoner

(10) Patent No.: US 11,554,440 B2
(45) Date of Patent: Jan. 17, 2023

(54) DIGITAL DISPLAY WELDING MASK WITH HDR IMAGING

(71) Applicant: Selene Photonics, Inc., San Leandro, CA (US)

(72) Inventor: Collin Stoner, San Leandro, CA (US)

(73) Assignee: Selene Photonics, Inc., San Leandro, CA (US)

( * ) Notice: Subject to any disclaimer, the term of this patent is extended or adjusted under 35 U.S.C. 154(b) by 26 days.

(21) Appl. No.: 17/230,968

(22) Filed: Apr. 14, 2021

(65) Prior Publication Data

US 2021/0316383 A1  Oct. 14, 2021

Related U.S. Application Data

(60) Provisional application No. 63/009,947, filed on Apr. 14, 2020.

(51) Int. Cl.
| | |
|---|---|
| B23K 9/095 | (2006.01) |
| A61F 9/06 | (2006.01) |
| G06T 19/00 | (2011.01) |
| H04N 5/235 | (2006.01) |
| G02B 27/01 | (2006.01) |
| B23K 9/32 | (2006.01) |

(52) U.S. Cl.
CPC ............ B23K 9/0956 (2013.01); A61F 9/065 (2013.01); B23K 9/0953 (2013.01); B23K 9/322 (2013.01); G02B 27/0172 (2013.01); G02B 27/0176 (2013.01); G06T 19/006 (2013.01); H04N 5/2355 (2013.01)

(58) Field of Classification Search
None
See application file for complete search history.

(56) References Cited

U.S. PATENT DOCUMENTS

| | | |
|---|---|---|
| 5,533,206 A | 7/1996 | Petrie et al. |
| 6,070,264 A | 6/2000 | Hamilton et al. |
| 8,248,324 B2 | 8/2012 | Nangle |
| 8,300,111 B2 | 10/2012 | Iwane |
| 9,895,267 B2 | 2/2018 | Cole |
| 9,922,460 B2 | 3/2018 | Denis |
| 10,448,692 B2 | 10/2019 | Hsu |
| 2007/0081250 A1 | 4/2007 | Garbergs |
| 2009/0231423 A1 | 9/2009 | Becker et al. |
| 2013/0291271 A1 | 11/2013 | Becker |
| 2014/0300769 A1 | 10/2014 | Lachapelle |

(Continued)

OTHER PUBLICATIONS

U.S. Appl. No. 17/230,966, Non-Final Office Action dated Sep. 22, 2022, 22 pp.

(Continued)

*Primary Examiner* — Talha M Nawaz
(74) *Attorney, Agent, or Firm* — PCFB Attorneys at Law; Justin K. Flanagan

(57) ABSTRACT

A display system for a welding helmet that includes a darkening filter layer, a high-dynamic range (HDR) camera system to capture an HDR light field, and an optical image stabilization subsystem. Captured images are displayed on an HDR electronic display within the welding helmet without risk of overexposure of ultraviolet radiation to the operator. In some examples, dual electronic displays are used to display different HDR images to each eye of the operator.

18 Claims, 22 Drawing Sheets

(56) References Cited

U.S. PATENT DOCUMENTS

| | | |
|---|---|---|
| 2016/0125653 A1 | 5/2016 | Denis |
| 2016/0214200 A1 | 7/2016 | Beeson |
| 2016/0267806 A1 | 9/2016 | Hsu |
| 2017/0049361 A1 | 2/2017 | Tanimura |
| 2017/0186230 A1 | 6/2017 | Ivers |
| 2018/0041684 A1 | 2/2018 | Hilldore |
| 2019/0253604 A1 | 8/2019 | Noda |
| 2020/0001388 A1 | 1/2020 | Sumner |
| 2020/0267296 A1 | 8/2020 | Usui |
| 2020/0374510 A1* | 11/2020 | Berends ............... H04N 13/239 |
| 2021/0086310 A1 | 3/2021 | Huh |
| 2021/0302749 A1* | 9/2021 | Law .................. G02B 27/0176 |
| 2021/0321028 A1 | 10/2021 | Stoner |
| 2021/0321074 A1 | 10/2021 | Stoner |

OTHER PUBLICATIONS

U.S. Appl. No. 17/230,969, Non-Final Office Action dated Jul. 27, 2022, 29 pp.

* cited by examiner

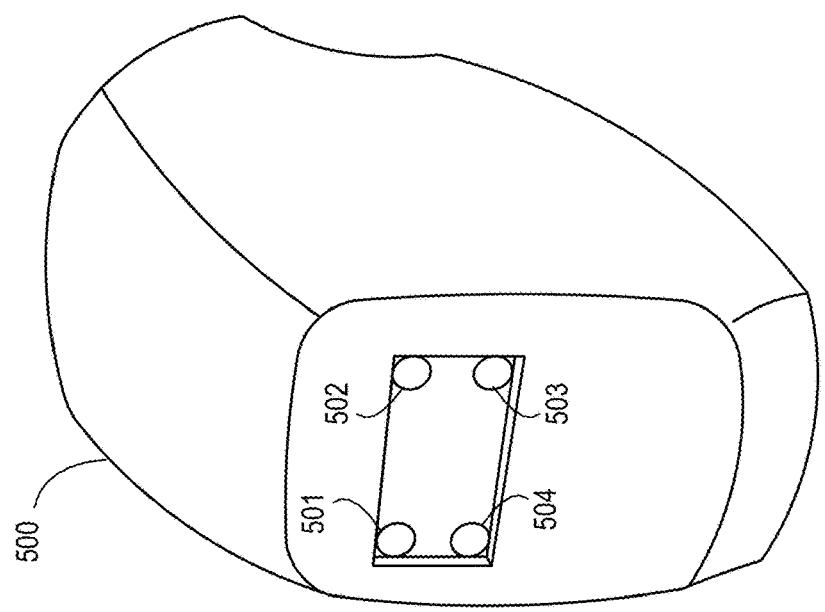
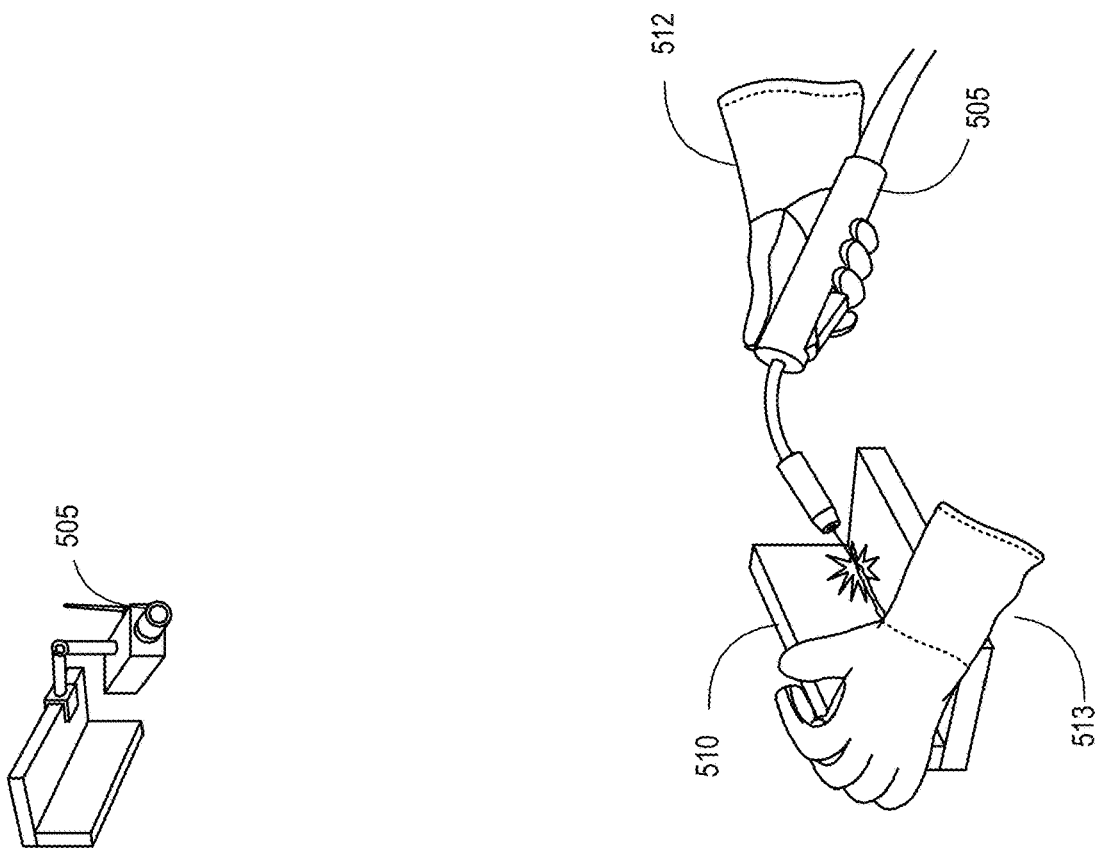
FIG. 5A

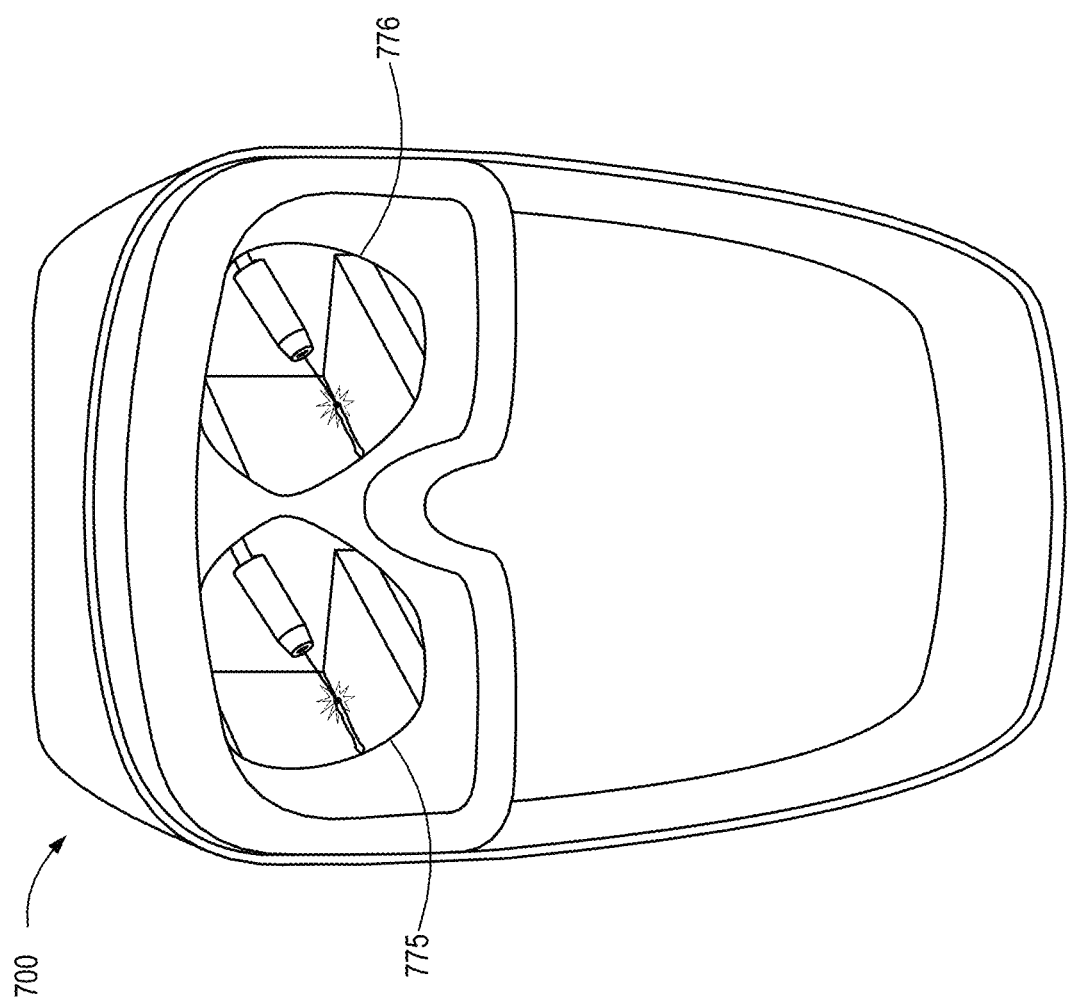

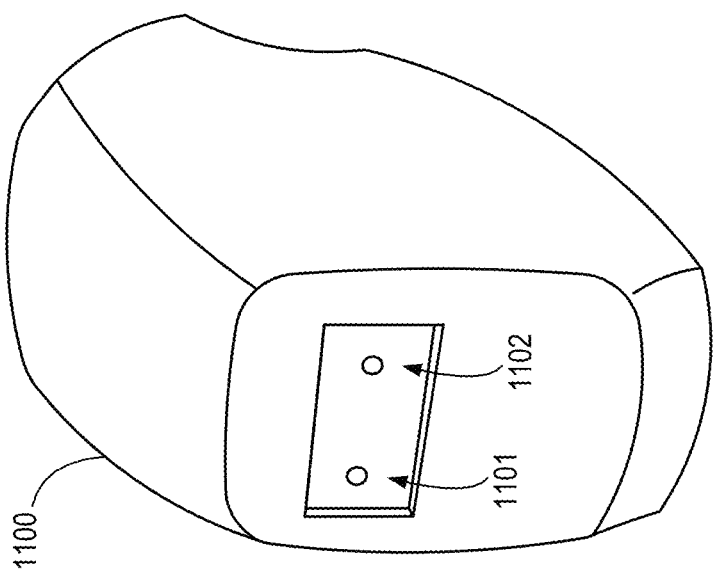
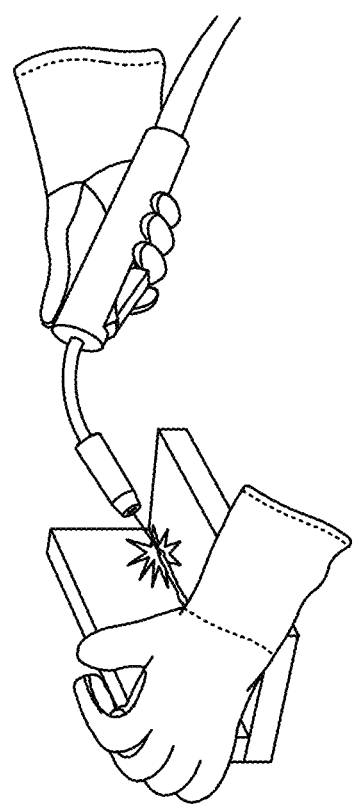
FIG. 11A

DIGITAL DISPLAY WELDING MASK WITH HDR IMAGING

RELATED APPLICATIONS

This application claims priority to U.S. Provisional Patent Application No. 63/009,947 titled Digital Display Welding Helmet with HDR Light Field Imaging, filed Apr. 14, 2020, which is hereby incorporated by reference in its entirety.

TECHNICAL FIELD

This disclosure relates to welding helmets and welding videography. In particular, this disclosure relates to video recording of welding activities and welding helmets that utilize an internal electronic display to display a work area to an operator of welding equipment.

BRIEF DESCRIPTION OF THE DRAWINGS

This disclosure includes illustrative embodiments that are non-limiting and non-exhaustive. Reference is made to certain of such illustrative embodiments that are depicted in the figures described below.

FIG. 5A illustrates a multi-camera welding mask with a connected remote camera, according to one embodiment.

FIG. 7 illustrates an example internal view of a welding mask with dual electronic displays, according to one embodiment.

FIG. 11A illustrates an example of a welding mask with light field cameras used to capture light fields for generating video feeds for each eye of an operator, according to one embodiment.

DETAILED DESCRIPTION

Figure 1:
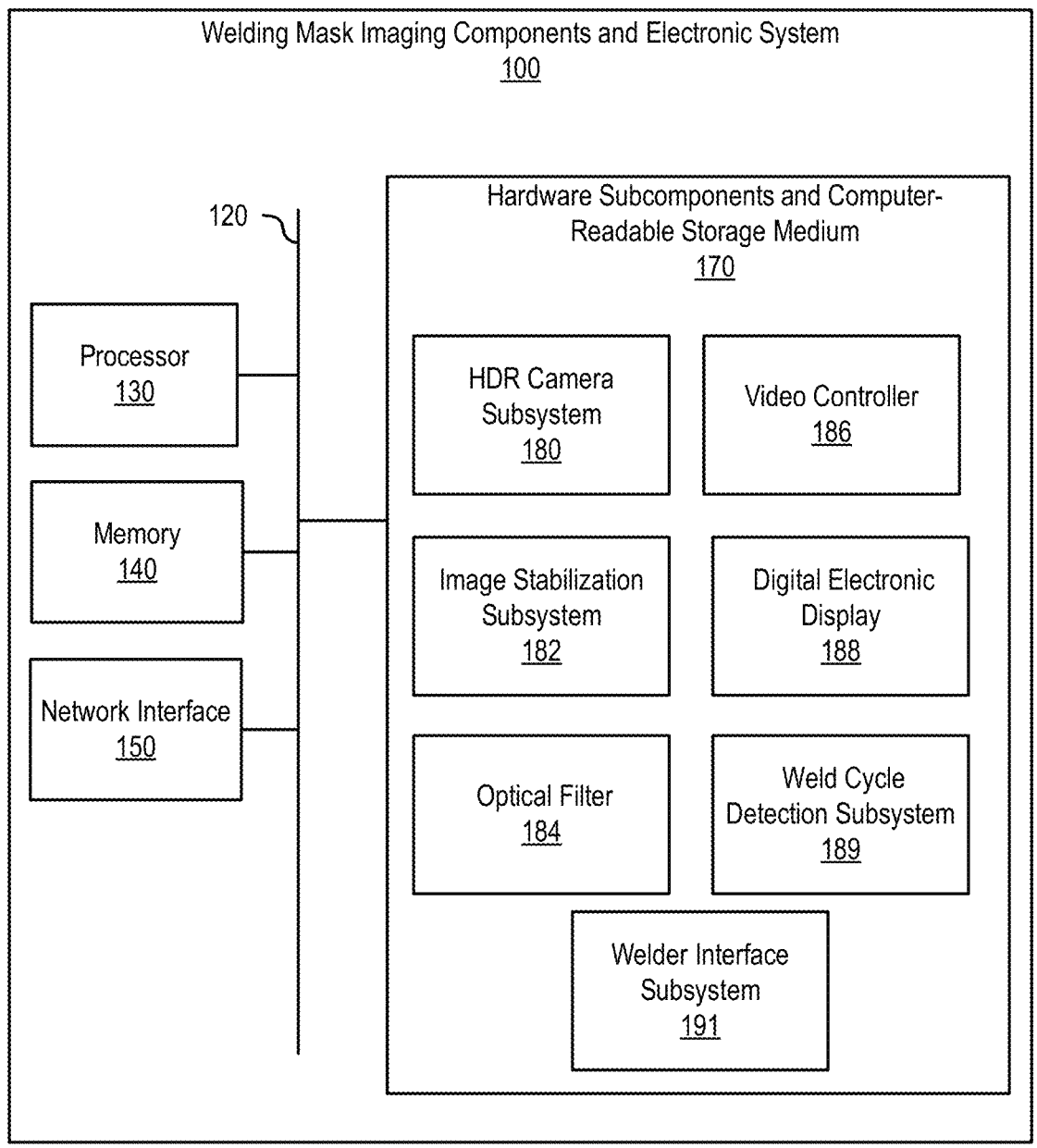
FIG. 1 illustrates a block diagram of example welding mask components, subsystems, and modules, according to one embodiment.

According to various embodiments of the presently described systems and methods, a welding mask is described that includes a high-dynamic range (HDR) camera subsystem to capture images with relatively long exposure and a darkening layer to attenuate light prior to image capture. For example, each frame of a video may be captured with an exposure time that is longer than one-half of a weld light intensity cycle of a welding machine (referred to herein as a "welder"). The darkening filter facilitates the long-exposure image captures by preventing overexposure. An optical image stabilization system (e.g., lens-based, software-based, or sensor-based) may be utilized to reduce or eliminate motion blur due to movement of the welding mask during the relatively long exposure time. Additional context, variations, and details of such a system are provided below.

Welding masks (including welding faceplates, helmets, hardhats, etc.) may be manufactured using plastic injection, plastic molding, metals, three-dimensional printing, computer numerical control (CNC) processes, etc. Traditional welding helmets include a window through which an operator may view the welding workplace. As used herein, the term "operator" encompasses individuals using the welding equipment (e.g., a welder) and users watching someone else using the welding equipment.

Thus, the presently described systems and methods apply to and may be incorporated as part of welding masks or another welding protection device used by a person welding or by other individuals nearby. Similarly, the presently described systems and methods may be incorporated as part of a video system to record the welding process. Any of the various described systems and methods may also be adapted for use in automated, robotic, or artificial intelligence (AI)-based welding systems. For instance, a video system of a robotic welding device may utilize the systems and methods described herein to generate an improved video feed for use by the robotic welding device. Accordingly, the term "welding mask" is understood to encompass any of a wide variety of protection and/or digital imaging devices used by an operator of a welder, bystanders, and/or robotic or other automated welding systems that may or may not need the protective elements of a welding mask.

As noted above, traditional welding helmets include a window with a darkening filter to reduce the intensity of the optical radiation generated by the workplace and/or reduce or even eliminate certain wavelengths (e.g., dangerous ultraviolet wavelengths and/or infrared wavelengths in the form of heat). Static or fixed darkening filters may make it easier and safer to view the workspace during a welding process. However, the static or fixed darkening filter may decrease the transmission of light to such an extent that the operator may not be able to see through the window when the operator is not welding. Some welding helmets include a pivotable window portion allowing the operator to raise the window when the operator is not welding and lower the window into place when the operator is welding.

Some welding helmets include auto-darkening filers (ADFs) that detect or respond to the increased optical radiation generated during welding (e.g., increased UV transmission). When the operator is not welding, the window may transmit sufficient light to allow the operator to view the workspace. When the operator begins welding, the window may respond by darkening and decreasing the transmissivity to a sufficient degree to protect the operator from overexposure and/or harmful wavelengths.

Static darkening filters may be cumbersome to use because they require the operator to reposition the welding mask in place to protect the operator each time the welding equipment is used. Automatic darkening filters respond to the instantaneous increase in optical radiation (or at least some wavelengths of increased optical radiation) when the welding equipment is used. Even when measured in microseconds or milliseconds, the response time delay of existing automatic darkening filters may expose the operator to bright light and/or harmful wavelengths for a brief period of time.

According to various examples of the presently described systems and methods, the window of a welding helmet may be replaced with an HDR camera subsystem and electronic display system. Specifically, the welding helmet may include a darkening filter to reduce the intensity of incident optical radiation and/or filter target wavelengths (e.g., ultraviolet and/or infrared wavelengths). In some embodiments, multiple darkening filters may be utilized. In some embodiments, automatic or light-detecting darkening filters may be utilized.

In various embodiments, an HDR camera subsystem captures images of the workspace and transmits electronic image data to an image processing subsystem. The image processing subsystem drives an electronic display within the welding helmet to display the captured images of the workspace to the operator. In some embodiments, dual electronic displays are utilized to display different images to each eye of the operator. The HDR camera subsystem may include any number of lenses and imaging sensors. Multiple cameras may provide different views of the workspace that can be stitched or otherwise composited and/or provide different perspectives of the workspace to each electronic display viewed by the operator.

For example, images may be composited to make the operator's hands transparent to provide an unobstructed view of a welder wand, a workpiece, and/or a surrounding workspace. In some embodiments, the operator's hands, the wand of the welding equipment, and/or another visual obstruction, may be made transparent, translucent, or effectively removed from the images displayed to the operator. In some embodiments, welding gloves having markers and/or having identifiable colors may be utilized to make it easier or more efficient for the image processing subsystem to remove the operator's gloved hands from the displayed images.

In some embodiments, additional image sensors remotely positioned relative to the workspace and/or secured to the wand of the welding equipment may provide additional perspectives. In some embodiments, the additional image sensors may be used to stitch images together to make portions of the workspace transparent, translucent, or effectively removed from the images displayed to the operator.

In various embodiments, an optical filter (e.g., an auto darkening filter) attenuates the optical radiation to allow for exposure times much longer than would otherwise be possible. For example, a traditional camera sensor might capture frames of a video during the very bright welding process using exposure times on the order of 10 microseconds to 1 millisecond. The optical filter allows for exposure times to be used that are on the order of 5-30 milliseconds. The optical image stabilization system operates in conjunction with the imaging sensor to reduce motion blurring during the relatively long exposure times.

The traditional model of capturing images of bright scenes, such as a welding arc, is to decrease the exposure time. The welding arc is generated by the welder at an operational frequency (e.g., 100-400 Hz). If an exposure time (e.g., electronic or mechanical shutter) is too long, the image will be overexposed. If the exposure time is too short, the image will be underexposed. However, if the exposure time in a traditional imaging system is not synchronized with the operational frequency of the welding arc, aliasing and/or other artifacts may be introduced into the image set. For example, some images may be captured when the welding arc is in an "off" or relatively dim portion of the cycle, and other images may be captured when the welding arc is in an "on" or relatively bright portion of the cycle. The resulting video feed of images may appear to flicker or have very dark scenes. The stroboscopic aliasing of the images captured of the welding arc may result in an undesirable video feed that is difficult or even dangerous to use.

In some instances, the operational frequency of the welder may correspond directly to or even be equal to the weld light intensity cycle. For example, a welder driven with an alternating current may exhibit peak light intensity events that correspond to the negative and/or positive peaks of the alternating current. In other instances, the weld light intensity cycle may be different from the operation frequency of the welder. For example, the weld light intensity cycle may vary based on variations in weld material, the welding speed, the distance between the welding wand and the workpiece, environmental conditions, and/or other welding condition characteristics. Regardless, the term "weld light intensity cycle" is used herein to refer to the generally periodic variation in light intensity exhibited during the welding process (e.g., a stroboscopic or flickering between high intensity light and low or no light).

Traditional imaging sensors for a video feed may determine that images of the welding arc and surrounding workspace should be captured at, for example, $1/8000^{th}$ of a second. The camera may capture 60 such images per second for a 60-frame-per-second (FPS) video feed. In such an embodiment, each frame of the 60-FPS video feed was captured using an exposure time of $\frac{1}{8000}^{th}$ of a second. The exact exposure time used may depend on the aperture of the camera and the brightness of the scene. However, due to the brightness of the welding arc, the exposure time of each frame will generally be much shorter than $\frac{1}{60}^{th}$ of a second. The resulting stroboscopic aliasing results in an undesirable or even unusable video feed.

According to various embodiments of the systems and methods described herein, the HDR camera subsystem may include fixed shade darkening filters, auto-darkening filters, and/or tunable auto darkening filters, such as variable shade LCD filters, in front of the camera or cameras to attenuate the brightness of the welding arc. Images can then be captured for an entire $\frac{1}{60}^{th}$ of a second (relatively long exposure) and delivered as part of a 60-FPS video feed. The exact exposure time and frame rate of the video feed can be adapted for a particular application. For example, the images could be captured at $\frac{1}{50}^{th}$ of a second or $\frac{1}{75}^{th}$ of second, and the video feed could be provided at 24 FPS, 30 FPS, 60 FPS, or 120 FPS. As long as the exposure time of each image is long enough to include at least one "on" cycle of the welding arc (e.g., one-half of the weld cycle, weld light intensity cycle, and/or the operating frequency), stroboscopic aliasing can be avoided or entirely eliminated.

Thus, in a specific example, an HDR camera subsystem may expose the image sensor for a defined percentage of the video frame time. Thus, in a system in which the image sensor is exposed for 100% of the video frame time, a 60-FPS video feed may include 60 images captured for $\frac{1}{60}^{th}$ of a second each (16.6 milliseconds). In various embodiments, optical image stabilization (e.g., digital film stabilization, sensor shifting, lens shifting, or the like) may be utilized to reduce or eliminate any motion blurring due to movement of objects in the workspace and/or movement of the camera during the relatively long exposure time. Examples of suitable optical image stabilization techniques and systems include, but are not limited to, floating orthogonal lens shift systems, sensor-shift systems, orthogonal transfer charged couple device (CCD) or complementary metal-oxide semiconductor (CMOS) systems, and the like, including combinations thereof.

Thus, according to various embodiments of the presently described systems and methods, a welding helmet is described that includes a darkening layer to attenuate light prior to image capture, an HDR camera subsystem to capture images with an exposure time longer than one cycle of the operating frequency of the welding arc, and an optical image stabilization system to reduce or eliminate motion blur due to the relatively long exposure time.

The HDR camera subsystem may adjust an effective ISO or gain of a digital sensor and/or adjust an aperture of the camera to attain consistent exposure levels using constant long-exposure image capture. Alternatively, the HDR camera subsystem may capture images at target exposure levels by adjusting the aperture, ISO sensor gain, and/or exposure time of each frame, while ensuring that the exposure time of each frame is longer than one cycle of the operating frequency of the welding arc.

In some embodiments, the exposure time may be set at a significant percentage (e.g., more than 40%, 50%, etc.) of the video frame period. For example, for a 30-FPS video feed, each frame may be captured with an exposure time of approximately 33 milliseconds (for 100%) or approximately 16 milliseconds (for 50%). For a 60-FPS video feed, each frame may be captured with an exposure time of approximately 16.6 milliseconds (for 100%) or approximately 11.6 milliseconds (for 70%). While the specific exposure time may not be based on the operating frequency of the welding arc, the result is that each frame of the video feed is captured with an exposure time long enough to include one or more on-cycles of the welding arc. A metal inert gas (MIG) welder may, for example, include a welding arc operating at 100 Hz with a 10-millisecond cycle, with on-cycles occurring every 5 milliseconds. Video frames (images) captured with exposure times in excess of 5 milliseconds would include at least one on-cycle.

According to various embodiments, the HDR camera subsystem may utilize one or more imaging sensors with global electronic shutters, mechanical shutters, rolling electronic shutters, or the like. In various embodiments, the HDR camera subsystem may include any number of CCD and/or CMOS sensors. Digital film sensors, including digital film sensors with integrated optical image stabilization, may be utilized as well.

According to some embodiments of the systems and methods described herein, the HDR camera subsystem may, for example, include a camera to capture images at 120 or 240 frames per second (or higher) and then deliver only those frames that were captured with a desirable or target exposure level as part of a 30 or 60 FPS video feed. For instance, only captured images having a target or substantially uniform average brightness level may be included as part of the video feed.

In other embodiments, one or more cameras are utilized to capture some images having relatively short exposures and other images having relatively long exposures. The short-exposure (darker) and long-exposure (lighter) images may be combined to create hybrid exposure images or high-dynamic range images that can be used as the frames for a high-dynamic range video feed. High-dynamic range videos allow for darker portions of the workspace to appear relatively lighter and lighter portions of the workspace (e.g., the welding arc) to appear relatively darker.

In some embodiments, the HDR camera subsystem may include multiple imaging sensors that capture images of the workplace at different exposure levels. In some instances, different imaging sensors may be associated with darkening filters of varying attenuation, different effective sensor gain (ISO) values, different apertures, and/or different exposure times. Images at different overall brightness levels may be combined to generate a high dynamic range (HDR) image of the workspace. Multiple HDR images may be delivered as frames of a video feed to an internal display of the welding helmet.

As a specific example, the HDR camera subsystem may include five cameras for each eye of the operator (10 cameras total). Each of the five cameras may capture images at different exposure levels. In examples in which the capture frame rate is the same as the display frame rate, five captured images may be combined to form an HDR image that can be delivered as a video frame to the electronic display for one eye of the operator. In examples in which the capture frame rate is higher than the display rate, any number of captured images may be combined to form HDR images for delivery as video frames to one eye of the operator. In a specific embodiment, five cameras may be positioned on the welding helmet in the approximate location of each eye of the operator, for a total of 10 cameras.

In some embodiments, a relatively high frame rate (e.g., 120 FPS or 240 FPS) may be used to capture images of a workspace with a constant exposure, including a constant exposure time. The video feed provided to the operator of the welding helmet may view one or more LCD or other electronic displays at 30 or 60 FPS. Accordingly, multiple captured frames may be combined into a single frame of the delivered video feed. In some instances, a best captured frame (e.g., frame closest to a target exposure or brightness level or a frame with the least black/white clipping) may be selected to the exclusion of the other frames for delivery as part of the video feed. In other embodiments, multiple frames of a constant exposure time (but different exposures via different darkening filter levels, apertures, and/or sensor gain values) may be combined to form an HDR frame for delivery to the electronic display(s). In still other embodiments (as previously described), multiple frames of different exposure times (e.g., short exposure times and long exposure times) may be combined to form HDR frames for delivery to the electronic displays.

In yet another specific example, five cameras may be associated with each eye of the operator to capture images at 120 FPS. Two electronic displays may display video feeds (e.g., stereoscopic video feeds) to the eyes of the operator at 30 FPS. Accordingly, 20 captured images may be combined to form a single HDR image for each frame of the video feed delivered to each eye of the operator. As previously described, internal electronic displays, such as LCD and/or OLED displays, within the welding helmet may display the video feed to the operator. Stereoscopic displays may provide slightly different perspectives to each eye of the operator. The resulting video feed is effectively a three-dimensional view of the workspace.

In any of the various embodiments described herein, the electronic display(s) within the welding helmet may display images (e.g., HDR images of the workspace) that are augmented to provide additional information. For example, the video feed may be augmented to include information relating to the welding process, such as temperature readings, warnings, welding speed, tips, etc.

In some embodiments, additional sensors may provide additional information that may also be overlaid on the video feed. For example, an ultrasonic sensor system may detect the quality of the weld, and the video feed may be overlaid or otherwise augmented to include an indication of the weld quality. For example, a numerical value may be displayed within the video feed to indicate a weld quality or temperature. Alternatively, the weld in the video feed may be overlaid or augmented to include color overlays on the weld itself indicative of the weld quality, temperature, or other measurement data.

In still other embodiments, the camera system may include light field cameras (also known as plenoptic cameras) that capture information about the direction from which the light rays are received in addition to intensity information. Captured images that include the direction from which the light rays were received can be combined to form HDR images in which the intensity levels of received optical rays from different locations within the workspace are combined. Location-based HDR images (e.g., HDR images based on the angle of incidence at which the light rays are received) may be processed to form the frames of the video feed displayed via an LCD or OLED electronic display.

In various examples, after the light field is captured, software is used to reverse the light rays that each camera captured to their 'source' in 3D space. After reversing the light rays to determine their source in 3D space, a new virtual perspective is 'rendered' by combining different light rays from different cameras in various proportions. Because the different cameras contained different exposures, the final image used for each frame of the video possesses a much higher dynamic range than the source images alone.

As described herein, the high dynamic range scene created by the welding arc relative to the ambient light in the surrounding workspace may be very difficult to capture using standard camera systems. Accordingly, discrete image sensors placed in close proximity to one another (e.g., 1" or less) may be used to capture images of the scene simultaneously at various exposure levels that cover the total dynamic range of the scene. As described herein, each camera or imaging sensor captures a unique perspective of the scene at a unique exposure. The resulting set of these images, when combined with knowledge of each camera's position relative to the workspace, constitutes a light field as the resulting information defines the intensity and direction of light following from different parts of the scene.

Furthermore, in various embodiments, the HDR image formed from the multiple images may be virtually rendered from any perspective within the group of real cameras (e.g., the five cameras associated with each eye). While traditional light field cameras may capture images at the same exposure level, the proposed implementation in which normal image sensors arranged in close proximity capture the light field data at different exposure levels avoids the use of specialized optics or specialized sensors.

The different exposure levels of the cameras associated with each eye of the operator can be captured by using different levels of darkening filters for each image sensor, adjusting an aperture (e.g., via an iris), using sensors with different gains, using different f-stops, adjusting brightness sensitivity settings, adjusting exposure times, and the like. Captured images may be rendered using an FPGA, a GPU, specialized application specific integrated circuits, and/or artificial intelligence processing cores.

Some of the infrastructure that can be used with embodiments disclosed herein is already available, such as: general-purpose computers, microprocessors, lens systems, cameras, image sensors, batteries, power supplies, LCD displays, OLED displays, computer programming tools and techniques, digital storage media, and communications networks. A computer or processing system may include a processor, such as a microprocessor, microcontroller, logic circuitry, or the like. The processor may include a special purpose processing device, such as an ASIC, PAL, PLA, PLD, FPGA, or other customized or programmable device. The computer or processing system may also include a computer-readable storage device, such as non-volatile memory, static RAM, dynamic RAM, ROM, CD-ROM, disk, tape, magnetic, optical, flash memory, or other computer-readable storage medium.

Aspects of certain embodiments described herein may be implemented as using microprocessors, microcontrollers, general-purpose computers, industrial-computers, FPGAs, discrete electrical components, surface mount components, or ASICs. Aspects of certain embodiments described herein may be implemented as software modules or components. As used herein, a software module or component may include any type of computer instruction or computer executable code located within or on a computer-readable storage medium. A software module may, for instance, comprise one or more physical or logical blocks of computer instructions, which may be organized as a routine, program, object, component, data structure, etc. that perform one or more tasks or implement particular abstract data types.

A particular software module may comprise disparate instructions stored in different locations of a computer-readable storage medium, which together implement the described functionality of the module. Indeed, a module may comprise a single instruction or many instructions and may be distributed over several different code segments, among different programs, and across several computer-readable storage media. Some embodiments may be practiced in a distributed computing environment where tasks are performed by a remote processing device linked through a communications network. In a distributed computing environment, software modules may be located in local and/or remote computer-readable storage media. In addition, data being tied or rendered together in a database record may be resident in the same computer-readable storage medium, or across several computer-readable storage media, and may be linked together in fields of a record in a database across a network.

Some of the embodiments of the disclosure can be understood by reference to the drawings, wherein like parts are generally designated by like numerals. The components of the disclosed embodiments, as generally described and illustrated in the figures herein, could be arranged and designed in a wide variety of different configurations. Thus, the following detailed description of the embodiments of the systems and methods of the disclosure is not intended to limit the scope of the disclosure, as claimed, but is merely representative of possible embodiments. Well-known structures, materials, or operations are not shown or described in detail to avoid obscuring aspects of this disclosure. In addition, the steps of a method do not necessarily need to be executed in any specific order, or even sequentially, nor need the steps be executed only once, unless otherwise specified.

FIG. 1 illustrates a block diagram of example welding mask components, subsystems, and modules, according to one embodiment. As illustrated, welding mask imaging components and electronic system 100 may include a bus 120 that connects a processor 130, a memory 140, a network interface 150, and various hardware subcomponents and computer-readable storage medium modules 170.

The hardware subcomponents and computer-readable storage medium modules 170 may include one or more of an HDR camera subsystem 180, an image stabilization subsystem 182, an optical filter 184, a video controller 186, a digital electronic display 188, a weld cycle detection subsystem 189, and a welder interface subsystem 191.

The HDR camera subsystem 180 may, for example, include a multipixel digital imaging sensor to capture images as frames of a video. The HDR camera subsystem 180 may further include an integrated video controller and/or be connected to an external video controller. In some embodiments, the processor 130 may implement computer-executable instructions stored in a non-transitory computer-readable medium to implement the operations and functions described herein in connection with the video controller 186. The video controller 186 may cause the HDR camera subsystem 180 to capture each frame of the video with an exposure time selected as a function of a weld cycle of a welder (e.g., a weld light intensity cycle, and/or the operating frequency). For example, the exposure time may be selected as a percentage of the weld cycle (e.g., as a percentage of the weld light intensity cycle). In various embodiments, the exposure time is selected to include at least one half of a weld cycle or weld light intensity cycle of the welder to ensure that at least one peak illumination event by the weld arc is captured during the exposure. In some instances, the exposure time may be selected as a complete duration of each frame of the video.

Specific examples of possible frame rates and exposure times include but are not limited to 24 frames per second with an exposure time of at least 40 milliseconds, 30 frames per second with an exposure time of at least 33 milliseconds, 48 frames per second with an exposure time of at least 20 milliseconds, 60 frames per second with an exposure time of at least 16 milliseconds, and 120 frames per second with an exposure time of at least 8 milliseconds. In some instances, the exposure times may be decreased slightly to accommodate for data transmission, storage, and processing times. For example, a 100% exposure time for a frame rate of 60 frames per second would mathematically 16.66 milliseconds, however the system may utilize a 84-90% exposure time of 14 or 15 milliseconds to allow some time for data transmission, storage, and processing.

Accordingly, some additional possible frame rates and exposure times include, but are not limited to 24 frames per second with an exposure time of at least 38 milliseconds, 30 frames per second with an exposure time of at least 31 milliseconds, 48 frames per second with an exposure time of at least 18 milliseconds, 60 frames per second with an exposure time of at least 14 milliseconds, and 120 frames per second with an exposure time of at least 6 milliseconds.

As noted above, traditional imaging approaches that utilize short exposures must be synchronized with the weld cycle (operational frequency) to avoid stroboscopic aliasing. The approach described herein, including in conjunction with FIG. 1, can be implemented as an asynchronous video capture system that captures frames of the video asynchronously with respect to the operating frequency of the welder. In some instances, the brightness of the light generated during each weld cycle is nonlinear with respect to current. In such embodiments, the video controller 186 may cause the HDR camera subsystem 180 to capture each frame of the video with an exposure time selected as a multiple of a half weld cycle or weld light intensity cycle of the welder to ensure that an equal number of peak illumination events are captured during each exposure. In some embodiments, the video controller 186 may cause the HDR camera subsystem 180 to capture each frame of the video with an exposure time selected to include multiple weld cycles or weld light intensity cycles of the welder, with an equal number of peak illumination events captured during each exposure.

In some embodiments, the video controller 186 may receive data identifying an operational frequency of the welder. For example, a welder interface subsystem 191 may be in communication with the welder (e.g., wired or wireless) and receive information identifying an instantaneous operation frequency and/or other welder operational information. The video controller 186 may use the data to select an exposure time as a submultiple of the identified operational frequency of the welder. In other embodiments, the system may include a weld cycle detection subsystem 189 to detect a duration of each weld cycle or weld light intensity cycle. The detected weld cycle or weld light intensity cycle information may be transmitted to the video controller 186 for use in selecting an exposure time.

According to various embodiments, the HDR camera subsystem 180 and the video controller 186 may capture light fields using light field cameras (e.g., plenoptic cameras). Alternatively, the light field data may be captured using a plurality of discrete image sensors placed in close proximity to one another (e.g., 1" or less) to capture images of the scene simultaneously at various exposure levels and at different perspectives that cover the total dynamic range of the scene.

In embodiments in which multiple discrete image sensors are used to capture the light field, computational processing is used to derive the light field data from the images captured by each image sensor based on each camera's relative position. The light field information can be processed to generate an HDR image that is virtually rendered from any perspective within the group of real cameras (e.g., the five cameras associated with each eye). While traditional light field cameras may capture images at the same exposure level, the proposed implementation in which normal image sensors arranged in close proximity capture the light field data at different exposure levels avoids the use of specialized optics or specialized sensors.

The image stabilization subsystem 182 may compensate for movement of the welding mask or other components during image capture. In some embodiments, the image stabilization subsystem 182 comprises an optical image stabilization lens system in which at least one lens element moves with respect to another lens element. In some embodiments, the image stabilization subsystem 182 comprises an image sensor stabilization subsystem in which the image sensor physically moves relative to a lens element of the digital imaging sensor.

The optical filter 184 attenuates at least some wavelengths of optical radiation (e.g., visible light, UV light, infrared light, etc.). The attenuation may be the same for all wavelengths or different depending on wavelength. For example, UV and infrared light may be effectively removed, while visible light may be attenuated sufficient for long-exposure imaging. In some embodiments, the optical filter is an auto-darkening filter (ADF). In some embodiments, the optical filter 184 is a tunable auto-darkening filter. The video controller 186 may tune the tunable auto-darkening filter to selectively attenuate the optical radiation to achieve a target exposure of each frame of the video for the selected exposure time.

The digital electronic display 188 may be positioned within a protective shell of the welding mask or in a remote location for viewing by remote persons and/or computerized and automated welding machines. In various embodiments, the digital electronic display 188 is positioned within the welding mask and displays the video of the welding process to the operator.

In some embodiments, the video controller 186 may implement functions of a video processing system. For example, the video controller 186 may be or include a video processing subsystem to generate digitally rendered composite video using multiple frames of videos from multiple cameras. For example, the video controller 186 may digitally render a composite video to form an augmented reality (AR) video with an informational overlay. A weld monitoring subsystem may detect welding characteristics of the welding process. The information overlay may display one or more of the detected welding characteristics. For example, the informational overlay in the composite AR video may display a weld pool size, a welding current, a visual indicator to direct the operator to speed up, an indicator to slow down, a suggestion to add material, a temperature, and/or a quality metric.

As previously described, variations of the imaging systems described herein may be utilized in conjunction with automated, robotic, or computerized welding systems. In such instances, the protective elements of the mask may be unnecessary. In such cases, the welding imaging system may include an HDR camera subsystem 180 with at least one camera to capture images as frames of a video. The HDR camera subsystem 180 may include or operate in conjunction with an optical filter 182 to attenuate at least some wavelengths of optical radiation generated by a welder during a welding process. The HDR camera subsystem 180 may include or operate in conjunction with an image stabilization subsystem 182 to compensate for movement of the welding mask during image capture by the HDR camera subsystem 180. A video processing subsystem may store the video in a data store (e.g., a database, server, data storage, etc.) and/or transmit the video to a remote location for viewing and/or processing.

Figure 2A:
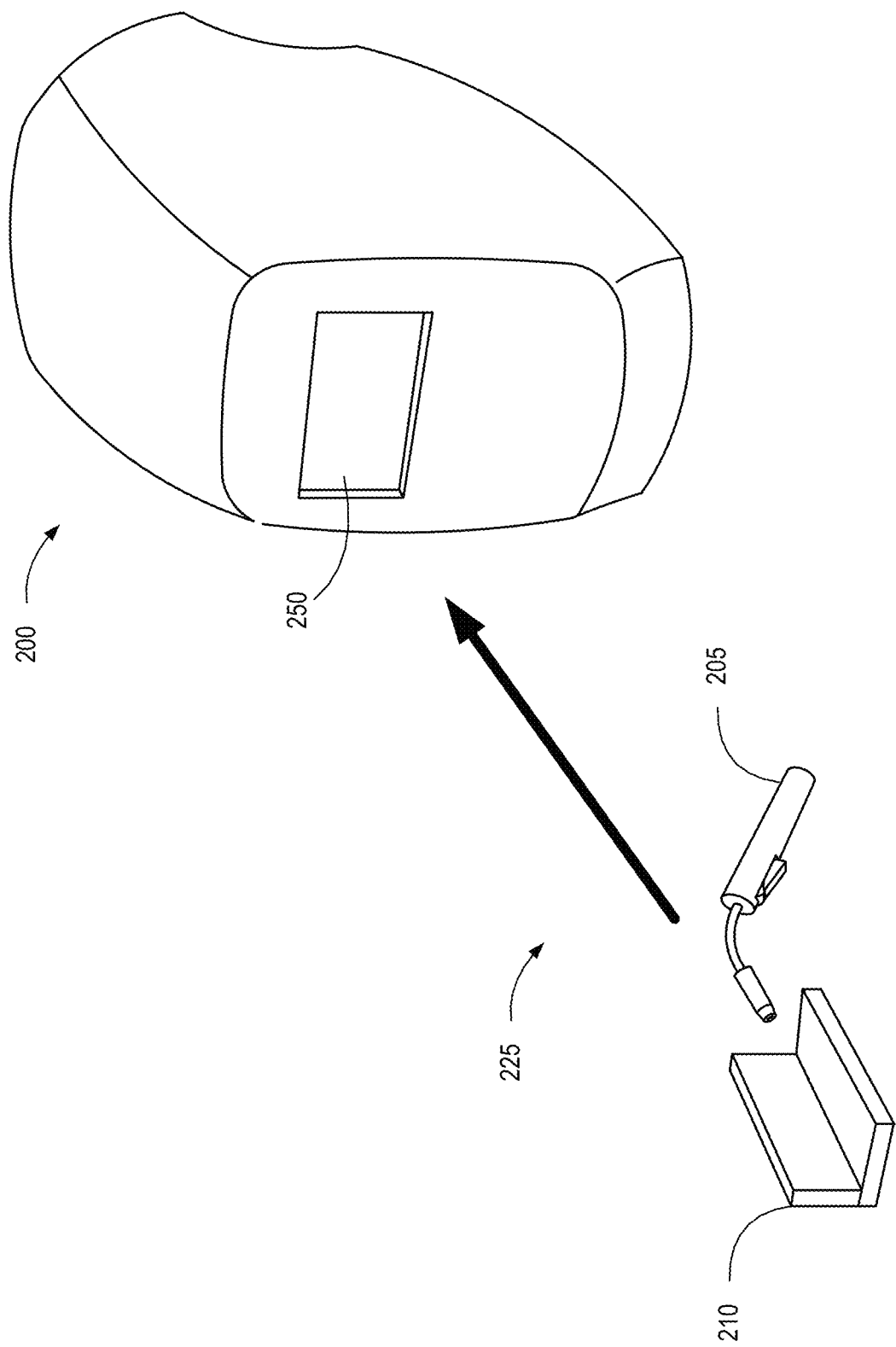
FIG. 2A illustrates an example of a welding mask receiving optical radiation during the welding of a workpiece, according to one embodiment.

FIG. 2A illustrates an example of a welding mask 200 receiving optical radiation 225 during the welding of a workpiece 210 (shown as two metal plates) by a welder 205 (only a welder wand is shown). Optical radiation 225 is incident on the window 250 of the welding mask 200. As described herein, instead of a traditional window 250, the welding mask includes a multi-layer imaging system that includes a darkening optical filter, an HDR camera subsystem to capture long-exposure images, and an image stabilization subsystem.

Figure 2B:
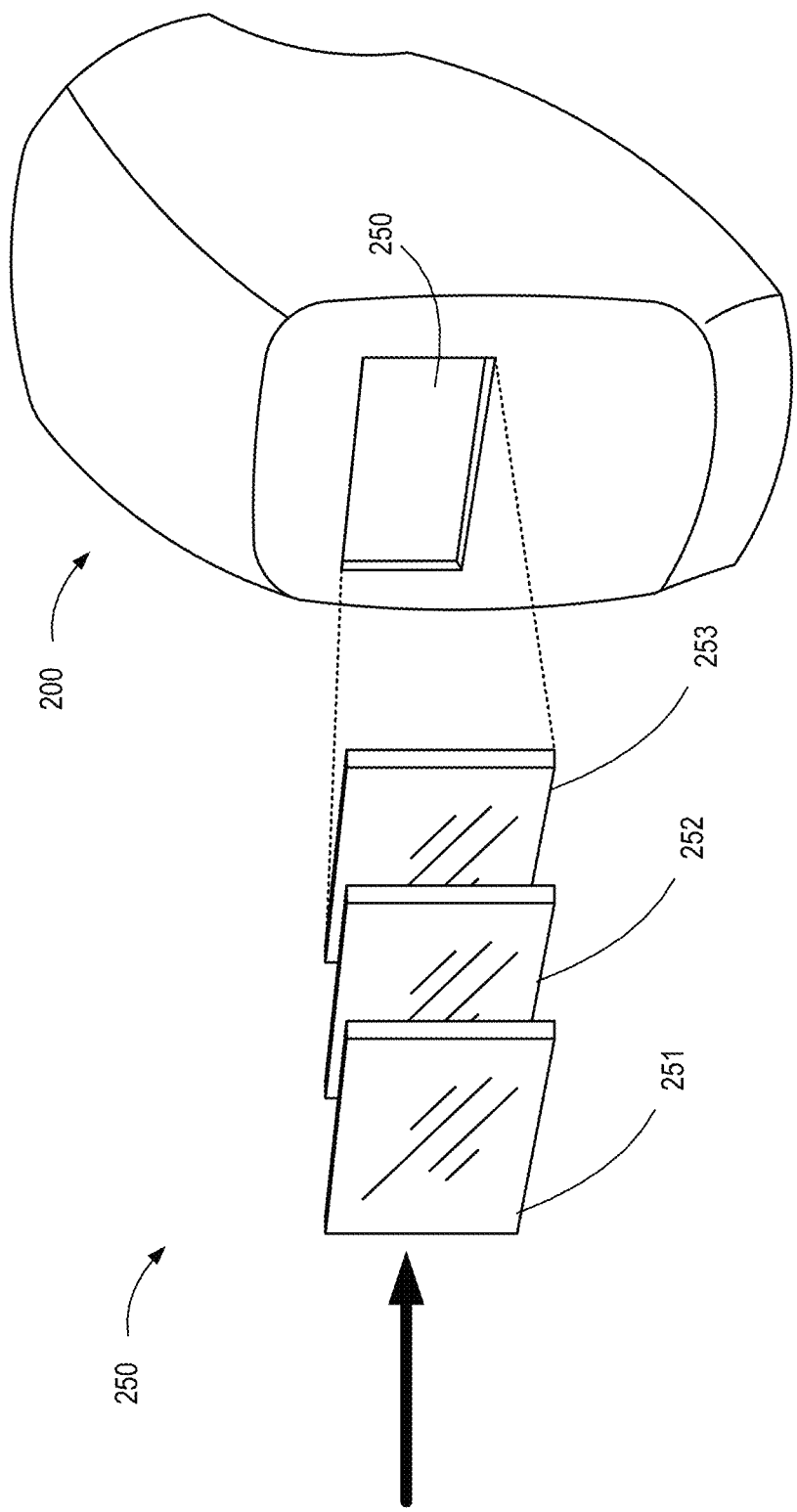
FIG. 2B illustrates an expanded view of three functional layers of a welding mask, according to various embodiments.

FIG. 2B illustrates an expanded view of three functional layers 251-253 of the "window" portion 250 of the welding mask 200, according to various embodiments. The three functional layers 251-253 may not be embodied as actual layers of a window. Instead, a first layer represents a darkening optical filter 251, such as an auto-darkening optical filter. A second layer represents an optical image stabilization layer 252. A third layer represents an HDR camera subsystem 253 that may include one or more cameras to capture relatively long exposures. Specifically, the images captured by the cameras can have exposure times longer than would otherwise be possible with the same sensors because of the initial darkening optical filter layer 251 and optical image stabilization layer 252.

Figure 2C:
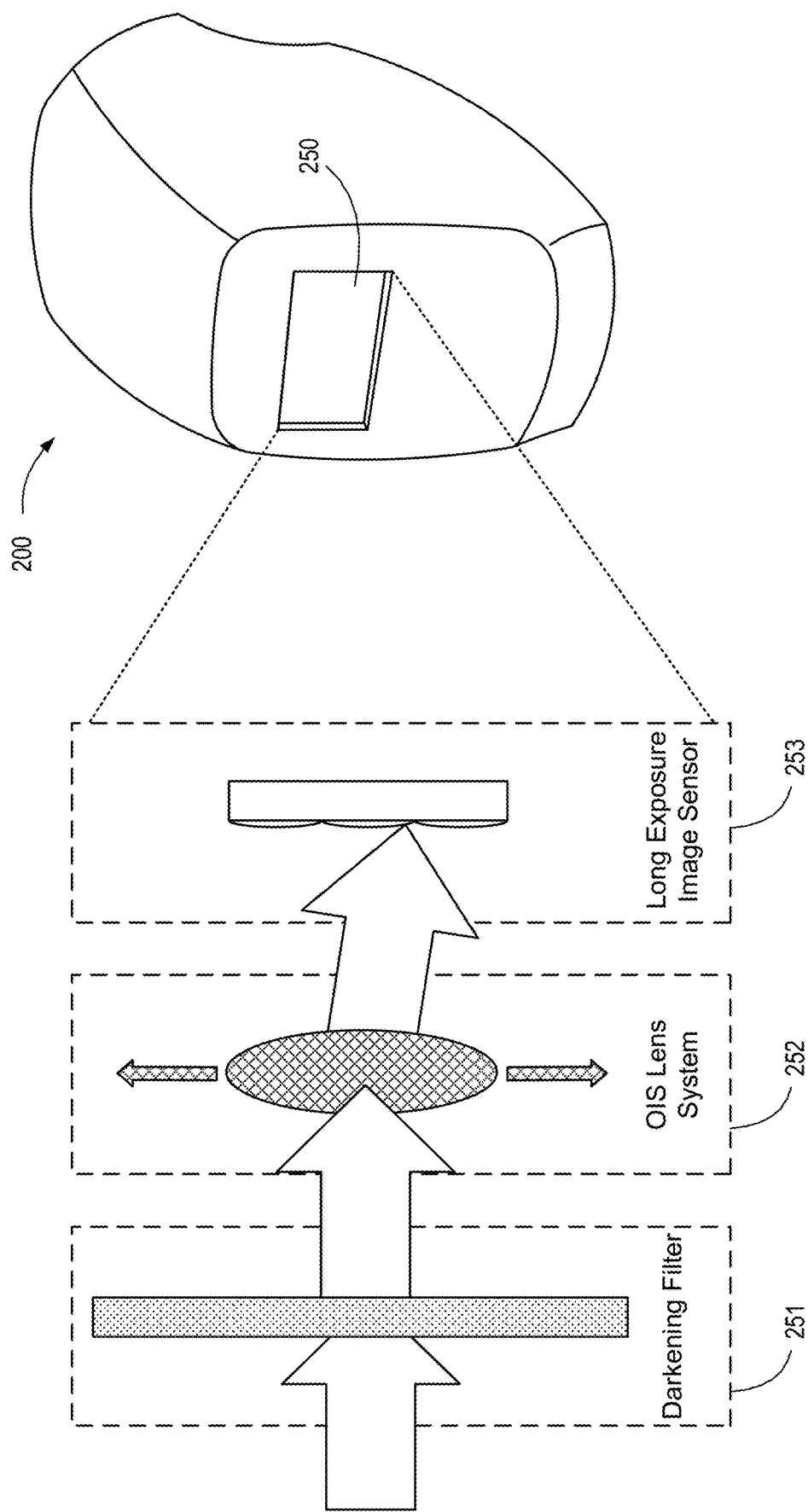
FIG. 2C illustrates a block diagram of three functional layers of a welding mask, according to various embodiments.

FIG. 2C illustrates a block diagram of the three functional layers 251-253 of the "window" portion 250 of the welding mask 200 described above. Specifically, the darkening filter 251 is illustrated as an initial layer to reduce the intensity of visible light generated by the welding arc and reduce or even eliminate the ultraviolet wavelengths. An optical image stabilization lens system 252 compensates for the motion of objects in the workspace and/or motion of the welding mask during image capture. Finally, a long-exposure image sensor of the camera subsystem 253 captures images having a relatively long exposure time, as described herein.

Figure 3A:
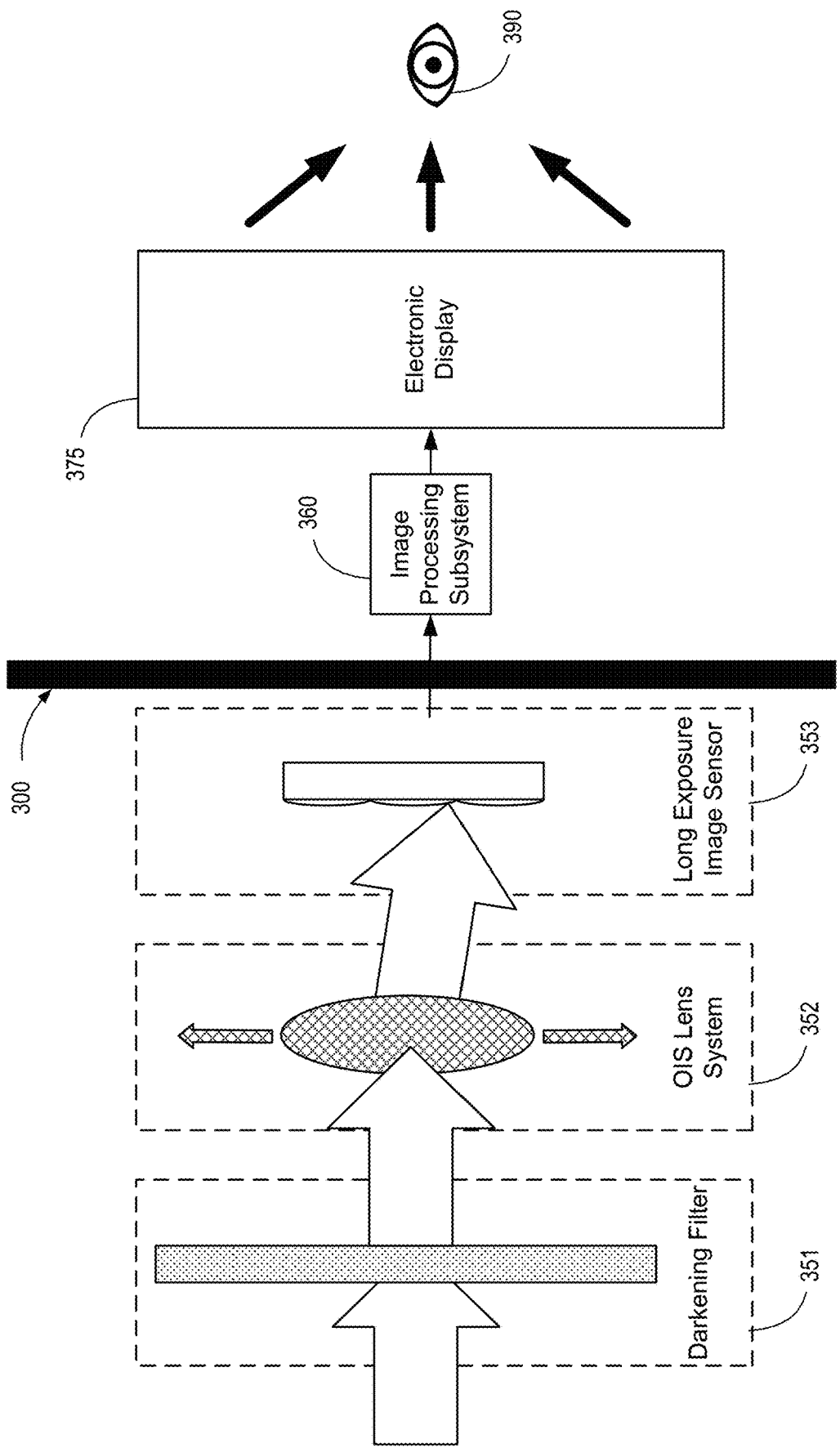
FIG. 3A illustrates a functional block diagram of a welding mask with long-exposure image capture and an electronic display, according to various embodiments.

FIG. 3A illustrates a functional block diagram of a digital display welding mask 300 with long-exposure image capture, according to various embodiments. As illustrated, a darkening filter 351, optical image stabilization lens system 352, and long-exposure image sensor 353 are used to capture images on one side of a welding mask 300 (illustrated as a black bar). Inside the mask 300 (to the right of the black bar), an image processing subsystem 360 may process the images (as described in conjunction with FIG. 1) and render them for display on an electronic display 375 visible by the eye 390 or eyes of the operator within the welding mask 300.

While many of the examples described herein are provided in the context of a welding mask 300 utilizing an internal electronic display 375, it is appreciated that the presently described systems and methods may also be utilized for video recording of welding activities. For example, a video camera may be used to capture video of a welding process. The welding video system may, for example, be part of a handheld device, a fixed or mounted recording system, and/or a portable video recording system. In some examples, the welding video system may be integrated as part of personal protection equipment (PPE). The welding video system may include any number of cameras and operate according to any combination of the various systems and methods described herein.

Figure 3B:
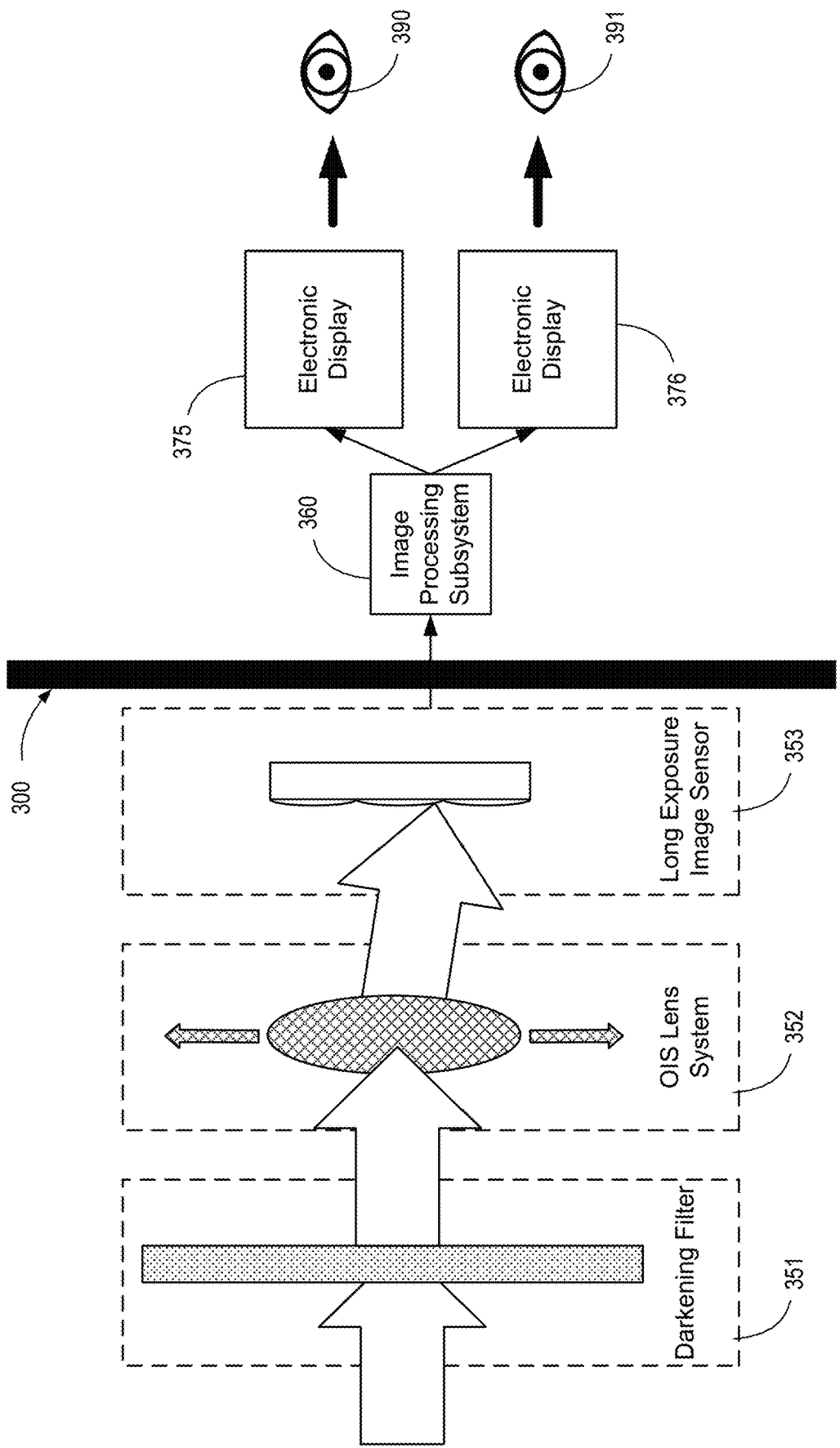
FIG. 3B illustrates a functional block diagram of a welding mask with long-exposure image capture and dual, digital displays, according to various embodiments.

FIG. 3B illustrates a functional block diagram of a dual-display digital welding mask 300 with long-exposure image capture, according to various embodiments. Again, a darkening filter 351, optical image stabilization lens system 352, and long-exposure image sensor 353 are used to capture images on one side of a welding mask 300 (illustrated as a black bar). Inside the mask 300 (to the right of the black bar), an image processing subsystem 360 may process the images (as described in conjunction with FIG. 1) and render them for display via two different electronic displays 375 and 376 (e.g., as a stereoscopic display) that provide images from slightly different perspectives to each eye 390 and 391 of the operator.

Figure 4:
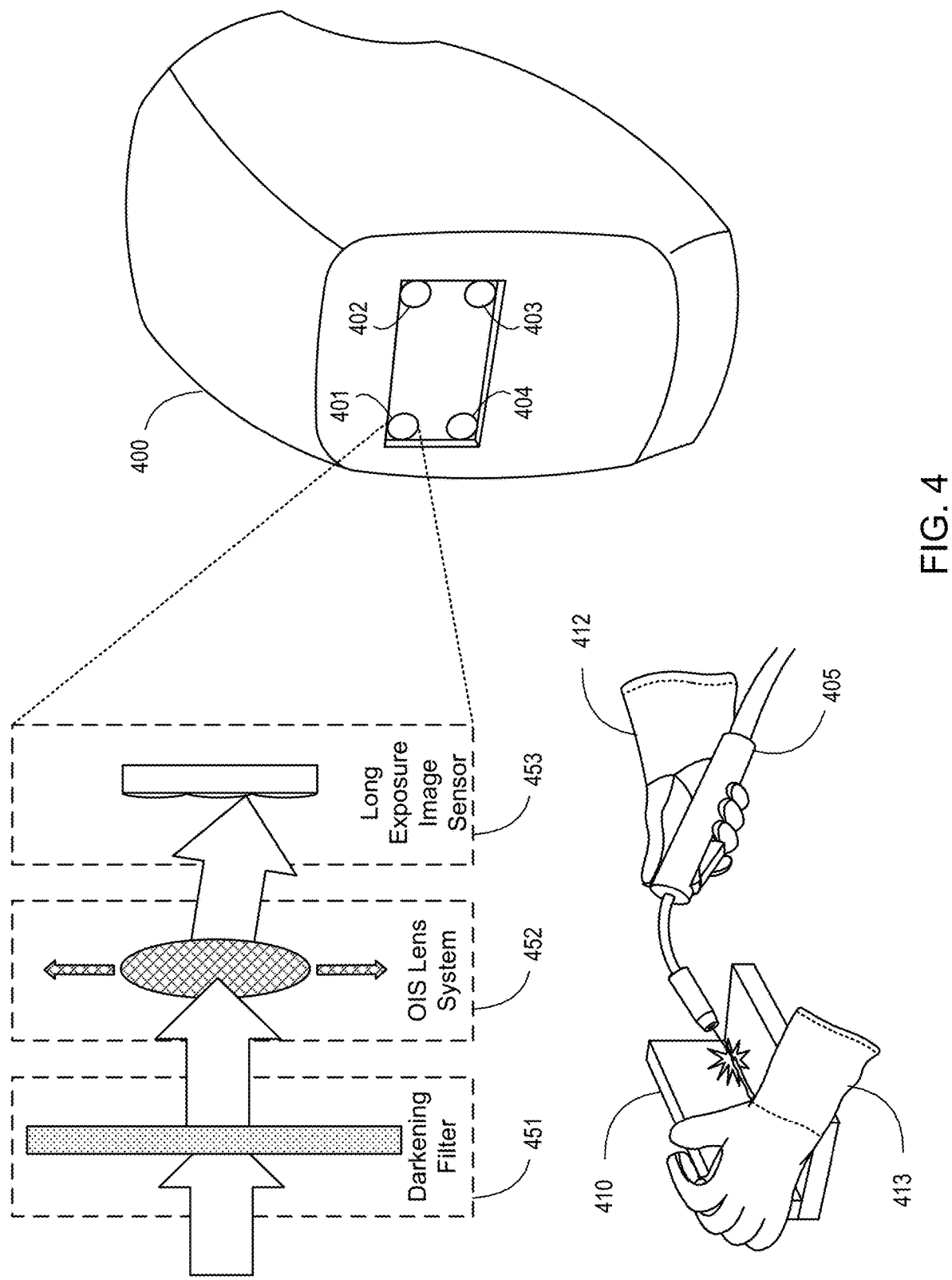
FIG. 4 illustrates a welding mask with multiple cameras that each include three functional layers, according to one embodiment.

FIG. 4 illustrates a multi-camera welding mask 400, each camera of which includes three functional layers, according to one embodiment. As illustrated, the multi-camera welding mask 400 includes four cameras 401, 402, 403, and 404. Each of the four cameras is associated with an individual darkening filter 451, optical image stabilizing lens system 452, and a long exposure image sensor 453. In some embodiments, a single or "global" darkening filter 451 and/or single or "global" optical image stabilizing lens system 452 may be utilized in conjunction with individual long exposure image sensors of the four cameras 401, 402, 403, and 404. The workpiece 410 may be imaged by the four cameras 401, 402, 403, and 404 during the welding process. The operator may hold the workpiece 410 with a left hand 413 and a welder wand 405 with a right hand 412.

The illustrated example of four cameras in a multi-camera welding mask 400 is merely one example of many possible camera arrangements. Any number of cameras may be utilized and positioned in various locations on or off (e.g., remotely) of the welding mask 400 to capture images, frames of a video, and/or provide a direct video feed from various perspectives relative to the workpiece 410 and welder wand 405.

FIG. 5A illustrates a multi-camera welding mask 500 with a connected remote camera 505, according to one embodiment. As illustrated, four cameras 501, 502, 503, and 504 may be positioned on the welding mask 500 to capture four perspectives of the workpiece 510 during the welding process by the welder wand 505. The remote camera 505 may be connected to the processing components and other electronics of the welding mask 500 (e.g., wirelessly or via a wire). The welding mask 500 may utilize the five video feeds to render composite video for display as part of a single video feed or as dual video feeds (e.g., stereoscopic video) to the operator.

The multiple on-mask cameras 501, 502, 503, and 504 and the remote camera 505 may provide different views of the workspace and workpiece 510 that can be stitched or otherwise composited. For example, images from the multiple cameras 501-505 may be composited to make the operator's hands 512 and 513 transparent to provide an unobstructed view of the welder wand 505, the workpiece 510, and/or the surrounding workspace. In some embodiments, the operator's hands 512 and 513, the welder wand 505, and/or another visual obstruction, may be made transparent, translucent, or effectively removed from the images displayed to the operator. In some embodiments, the operator may wear welding gloves having markers (e.g., lines, colors, stripes, QR codes, etc.) and/or having identifiable colors (e.g., green) that make it easier or more efficient for the welding mask 500 to remove the operator's gloved hands from the displayed images (e.g., frames of the video feed).

Figure 5B:
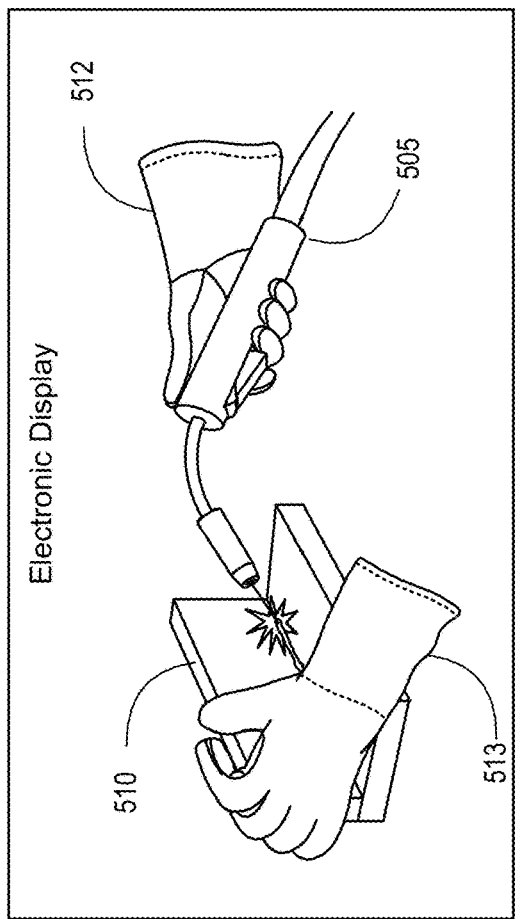
FIG. 5B illustrates a composite video generated by the multi-camera welding mask, according to one embodiment.

FIG. 5B illustrates a composite video on an electronic display 575 generated by the multi-camera welding mask 500 of FIG. 5A, according to one embodiment. In the illustrated embodiment, the workpiece is partially obstructed by the operator's left hand 513. The right hand 512 is visible gripping the welder wand 505.

Figure 5D:
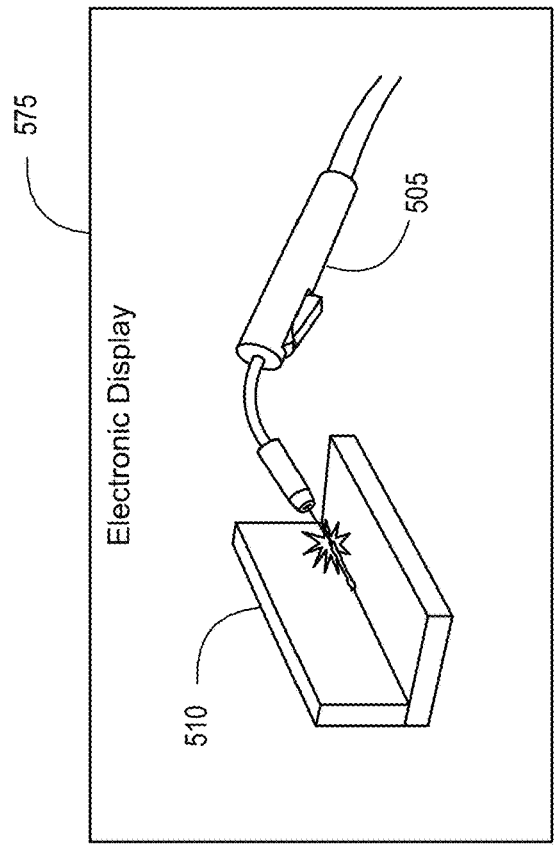
FIG. 5D illustrates an augmented composite video with the hands of the operator removed from the workpiece, according to one embodiment.
Figure 5C:
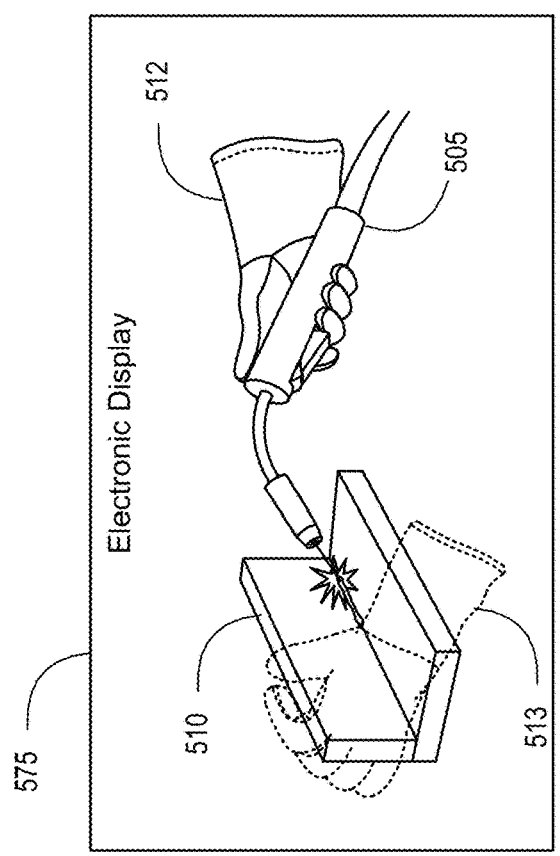
FIG. 5C illustrates an augmented composite video generated by the multi-camera welding mask with one hand of the operator shown partially transparent, according to one embodiment.

FIG. 5C illustrates an augmented composite video on the electronic display 575 generated by the multi-camera welding mask 500 of FIG. 5A. As illustrated, the left hand 513 of the operator is shown at least partially translucent so that the workpiece 510 can be viewed more clearly, according to one embodiment.

FIG. 5D illustrates an augmented composite video on the electronic display 575 with both hands 512 and 513 of the operator removed from the workpiece 510 and welder wand 505, according to one embodiment.

Figure 6A:
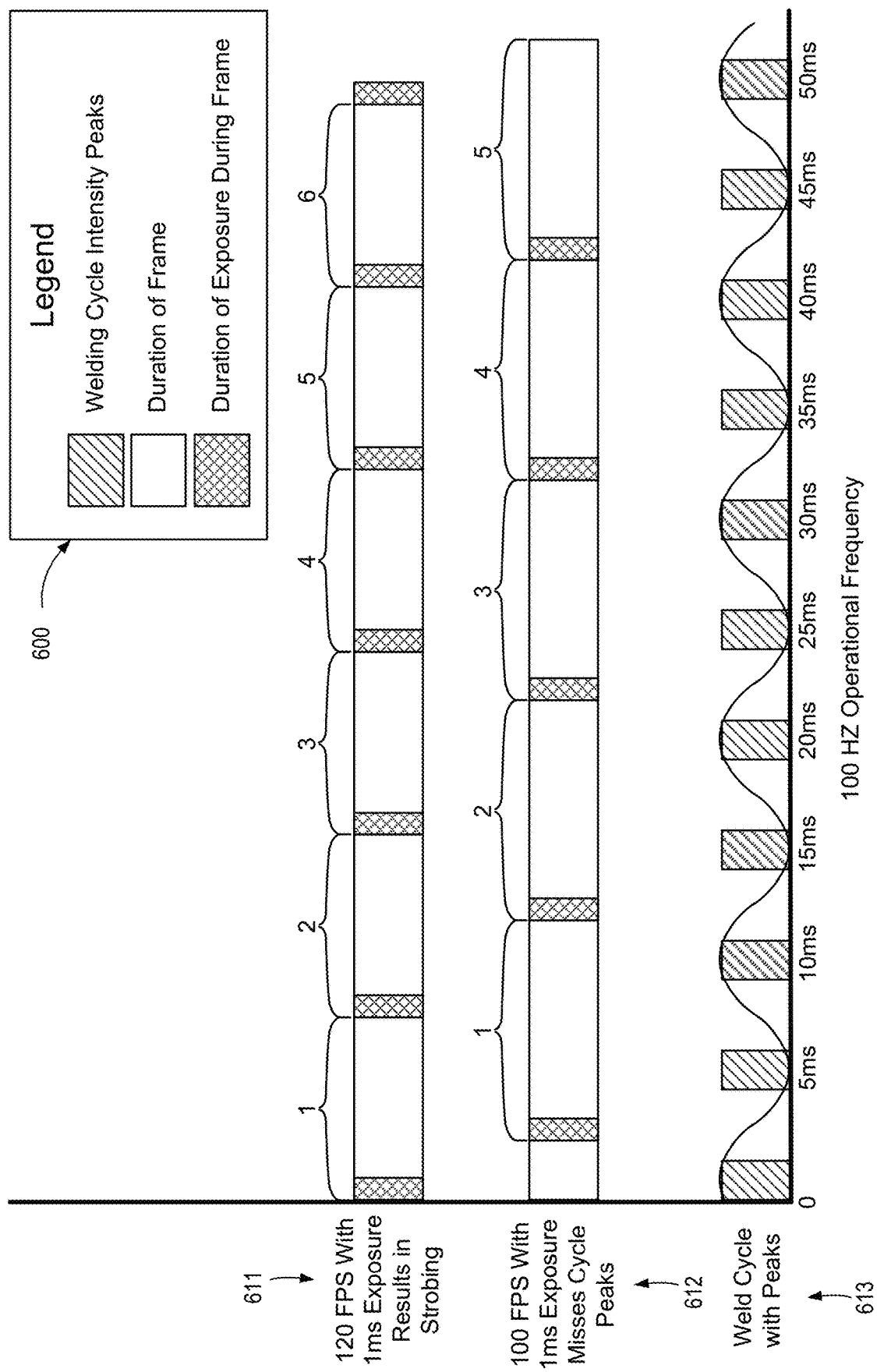
FIG. 6A illustrates examples of exposure times for capturing frames of a video, according to various embodiments.

FIG. 6A illustrates examples of exposure times for capturing frames of a video, according to various embodiments. A legend 600 identifies shading patterns for welding cycle intensity peaks, the duration of each frame, and the duration of exposure during each frame. The horizontal axis represents time on the scale of a 100 Hz operational frequency of a welder. As illustrated, the welder shows weld cycle intensity peaks 613 (e.g., peak brightness events) at positive and negative peaks every 5 milliseconds for the 10-millisecond wavelength.

The top graph shows an example of a 120 frame per second (FPS) video capture 611 with 1 millisecond exposures used for each frame. As illustrated, the exposure time of the first frame of the 120 FPS video capture 611 coincides with a weld cycle peak 613. However, due to a lack of synchronization and the short exposure time (e.g., less than one half of a weld cycle), the exposure time of the second frame of the 120 FPS video capture 611 is not aligned with a weld cycle peak 613. Accordingly, the second frame of the 120 FPS video capture 611 will be much darker than the first frame of the 120 FPS video capture 611. As such, the graph of the 120 FPS video capture 611 provides an example of a video capture approach that results in undesirable flickering or stroboscopic aliasing.

One possible approach to avoid the undesirable flickering or stroboscopic aliasing is to use a video frame rate that corresponds to the operational frequency of the welder. However, this approach requires that the relatively short exposure time be synchronized with the weld cycle peak 613. The graph of the 100 FPS video capture 612 shows relatively short, 1 millisecond exposure times. As illustrated, a lack of synchronization results in the exposure of every frame being offset with respect to the weld cycle peaks. The resulting video may be underexposed and/or not capture images of the weld arc at all.

Figure 6B:
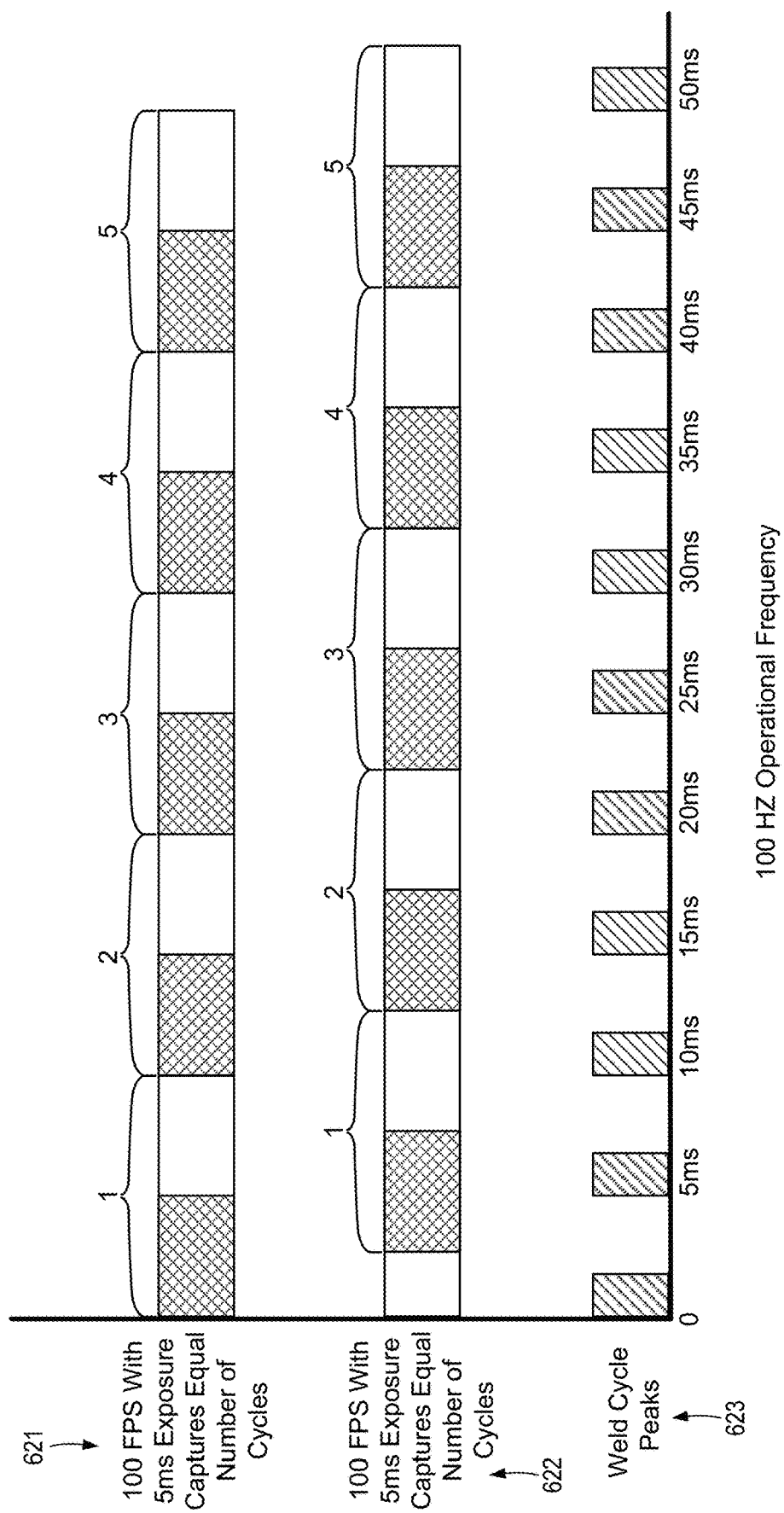
FIG. 6B illustrates additional examples of exposure times for capturing frames of a video, according to various embodiments.

FIG. 6B illustrates additional examples of exposure times for capturing frames of a video, according to various embodiments. According to various embodiments of the systems and methods described herein, relatively long exposures (e.g., exposures that are at least one half of a weld cycle or weld light intensity cycle) allow for improved video capture with correctly exposed frames without any flickering or stroboscopic aliasing. The graph of image capture at 100 FPS with 5-millisecond exposures 621 shows that that exposure of each of frames 1-5 includes exactly one complete weld cycle peak in the graph of weld cycle peaks 623.

The graph of asynchronous image capture at 100 FPS with 5-millisecond exposures 622 demonstrates that each exposure still includes one complete weld cycle peak. In some instances, the exposure may include a portion of one weld cycle peak and a portion of another weld cycle peak that additively equate to a single weld cycle peak.

Figure 6C:
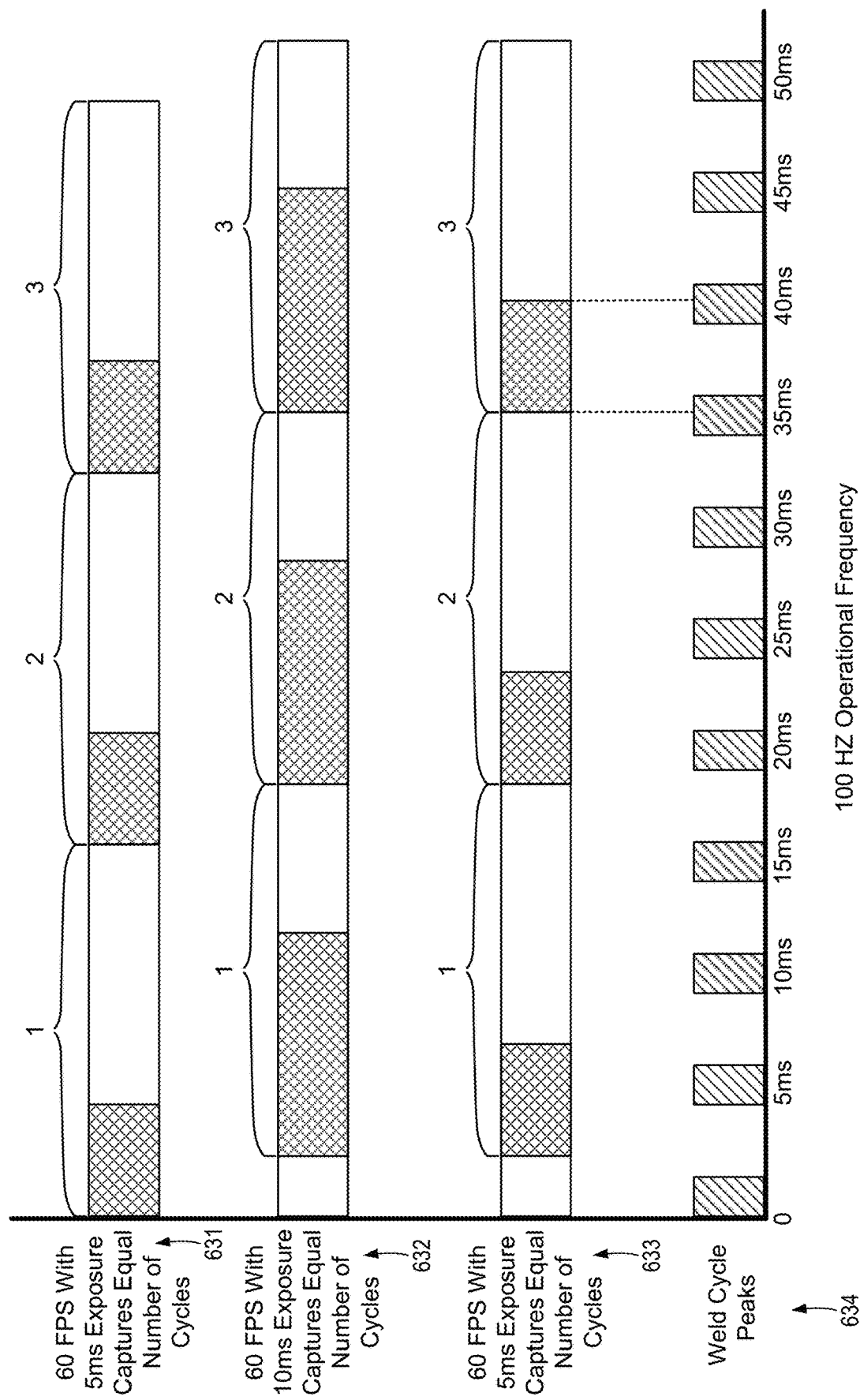
FIG. 6C illustrates additional examples of exposure times for capturing frames of a video, according to various embodiments.

FIG. 6C illustrates additional examples of exposure times for capturing frames of a video, according to various embodiments. As illustrated, a 60 FPS video capture with 5-millisecond exposures 631, a 60 FPS video capture with 10-millisecond exposures 632, an offset or asynchronous 60 FPS video capture with 5-millisecond exposures 633 all include frames with an equal number of weld peak cycles 634. Accordingly, each of these relatively long-exposure video capture schemas allows for a flicker-free video.

Figure 6D:
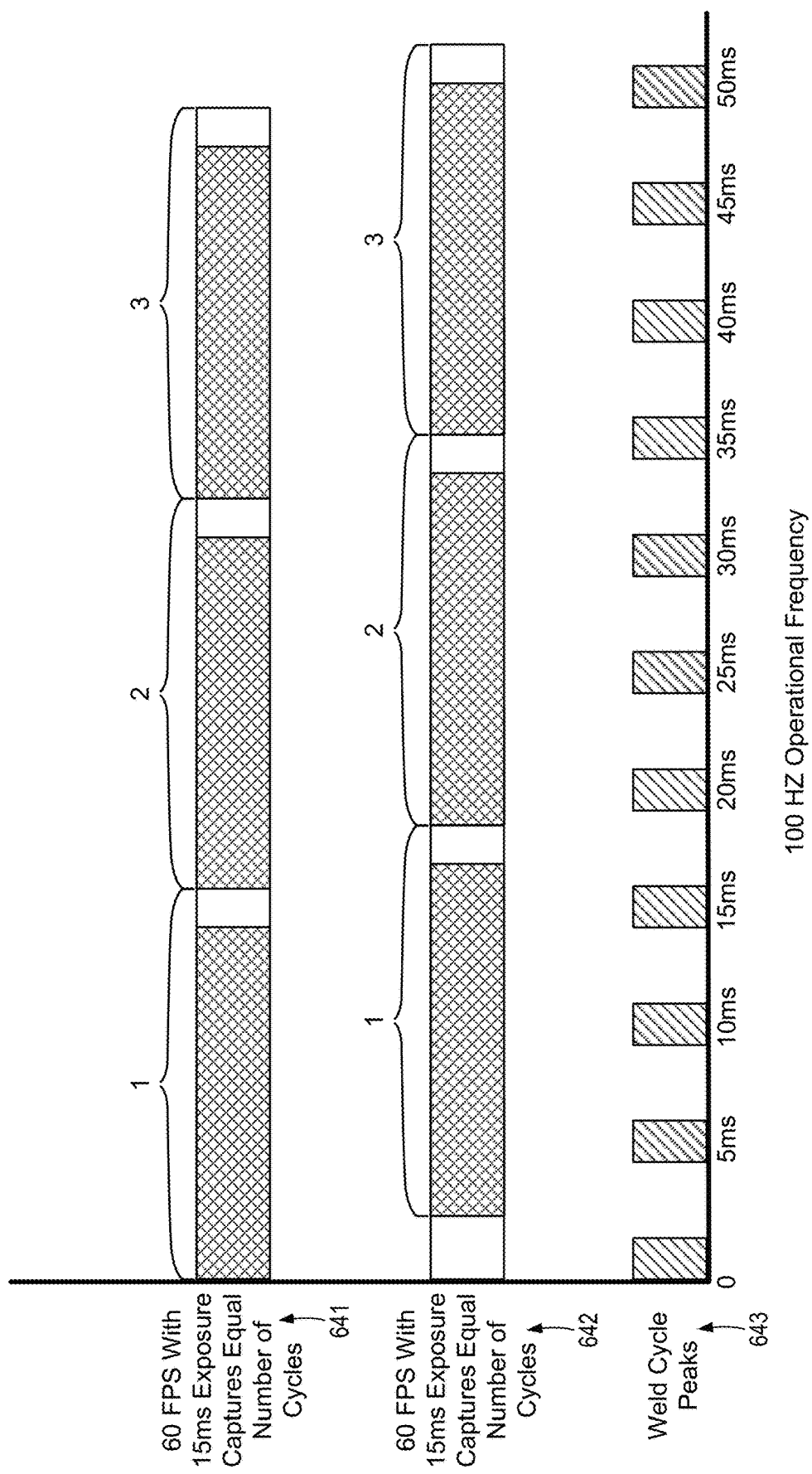
FIG. 6D illustrates additional examples of exposure times for capturing frames of a video, according to various embodiments.

FIG. 6D illustrates additional examples of exposure times for capturing frames of a video, according to various embodiments. Again, weld cycle peaks 643 for a 100 Hz operation frequency are illustrated along the horizontal time axis. A synchronized 60 FPS video capture with 15-millisecond exposures 641 is illustrated in which each frame includes three weld cycle peaks. The relatively long exposure ensures that synchronization is unnecessary. Accordingly, asynchronous 60 FPS video capture with 15-millisecond exposures 642 also captures 3 weld cycle peaks in each frame.

FIG. 7 illustrates an example internal view of a welding mask 700 with dual electronic displays 775 and 776, according to one embodiment. In some embodiments, the dual electronic displays 775 and 776 may display stereoscopic images to the operator that allow for three-dimensional rendering of the welding process.

Figure 8:
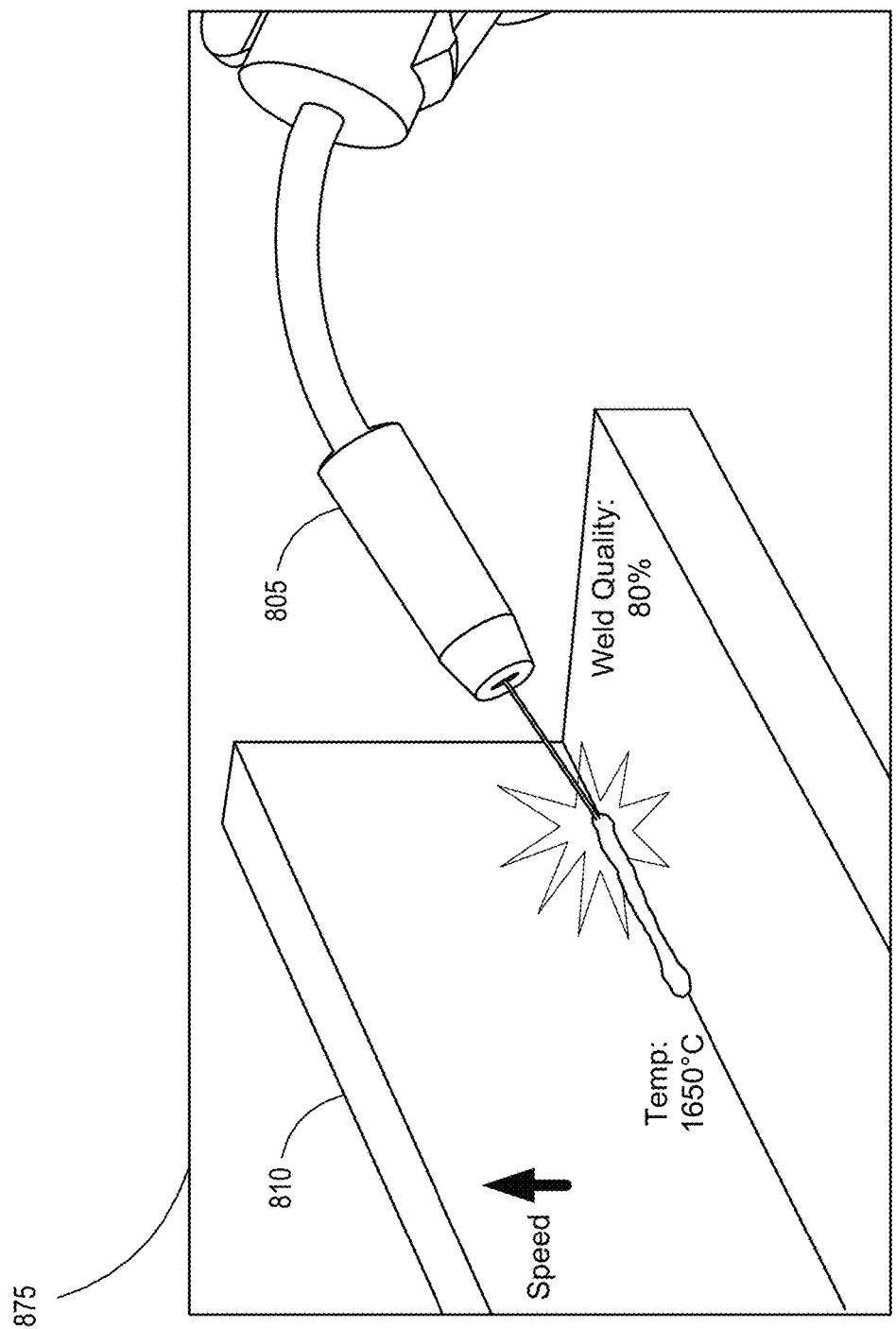
FIG. 8 illustrates an augmented video generated by the welding mask with informational overlay elements, according to one embodiment.

FIG. 8 illustrates an augmented video generated by the welding mask and displayed within an electronic display 875. The augmented video may include "real" elements, such as the workpiece 810 and a weld wand 805 with informational overlay elements, according to various embodiments. In the illustrated example, the informational overlay includes a speed arrow suggesting that the operator increase the welding speed. A temperature sensor may detect a weld temperature and the temperature may be overlaid as part of the informational overlay. Additionally, a weld quality indicator indicates that the weld quality is 80%.

For example, a weld monitoring subsystem may monitor the weld based on visual appearance, ultrasonic density monitoring, weld temperature consistency, and/or the like. The weld quality indicator may indicate a weld quality based on one or more weld characteristics being within a threshold range of an optimal value. The weld quality metric may be overlayed on the video feed as a percentage, a "good" or "bad" annotation, a star rating, a numerical value, a letter grade, a bar graph, and/or the like.

Figure 9A:
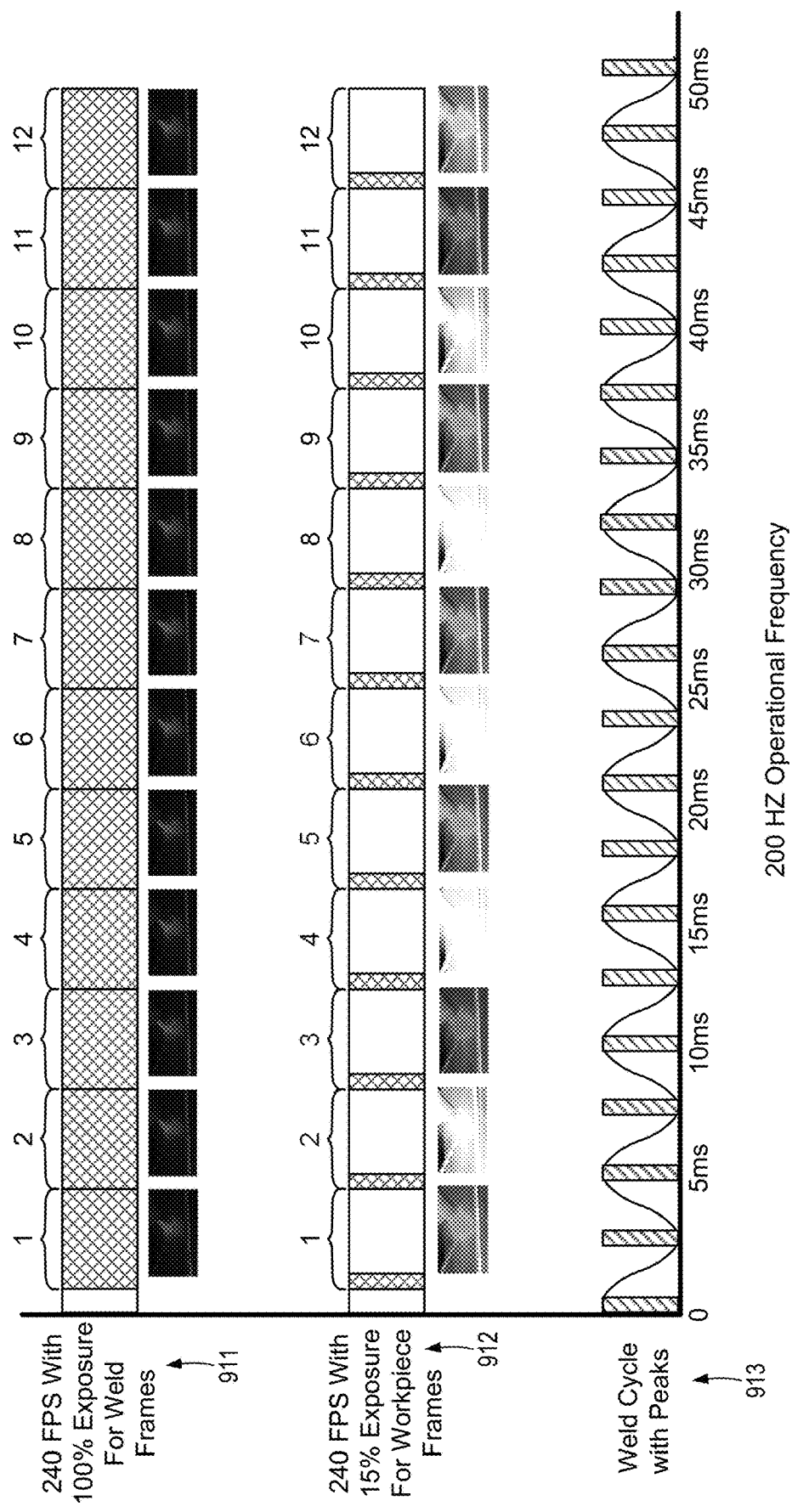
FIG. 9A illustrates high frame rate video capture at various exposure levels for high dynamic range (HDR) frame compositing, according to one embodiment.

FIG. 9A illustrates high frame rate video capture at various exposure levels for HDR frame compositing, according to one embodiment. The illustrated embodiment includes weld cycle peaks 913 of a welder operating at a 200 Hz operational frequency. While any of a wide variety of specific frame rates may be used for image capture and/or video delivery, the illustrated example utilizes 240 FPS. A first video capture at 240 FPS 911 with an exposure time equal to 100% of the frame duration may be utilized to image the weld arc. The workpiece and surrounding work area may appear very dark in the image due to the other exposure settings (e.g., the ISO equivalent, aperture, and associated darkening optical filter). A second video capture at 240 FPS 912 with an exposure time equal to only 15% of the frame duration may be used to image the workpiece and/or surrounding work area.

As illustrated, the imaging frame rate of 240 FPS 912 is not synchronized with the welder operational frequency of 200 HZ. Accordingly, frames 1, 5, 7, and 9 are moderately exposed, frames 2, 4, 6, 8, and 10 are overexposed, and frames 3 and 11 are underexposed. Those frames that correctly expose the workpiece and/or surrounding work area may be combined with the images of the weld arc from the first video capture at 240 FPS 911 to generate HDR images. Those frames that are overexposed or underexposed may be discarded or used to further extend the range of the HDR images.

Figure 9B:
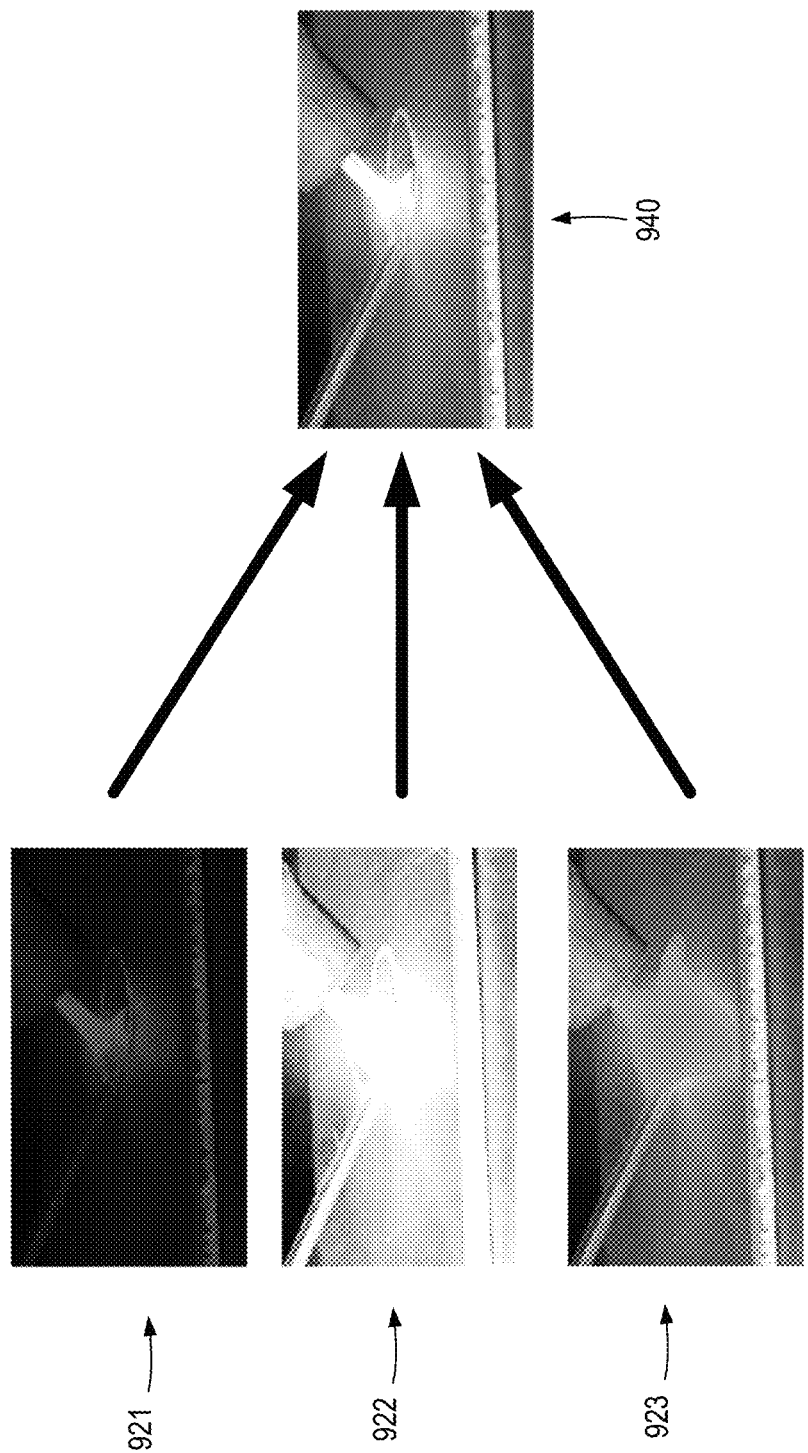
FIG. 9B illustrates a simplified block diagram of an HDR frame formed from three base images at different exposure levels, according to one embodiment.

FIG. 9B illustrates a simplified block diagram of an HDR frame 940 formed from three base images 921, 922, and 923 at different exposure levels, according to one embodiment. The HDR approach illustrated in FIG. 9B in which multiple images are combined to generate an HDR image may be utilized. However, as described herein, multiple image sensors may be utilized to calculate or generate light field data. Rather than combining images from the image sensors to generate an HDR image, the system may directly generate an HDR frame for the HDR video using the light field data.

Figure 10A:
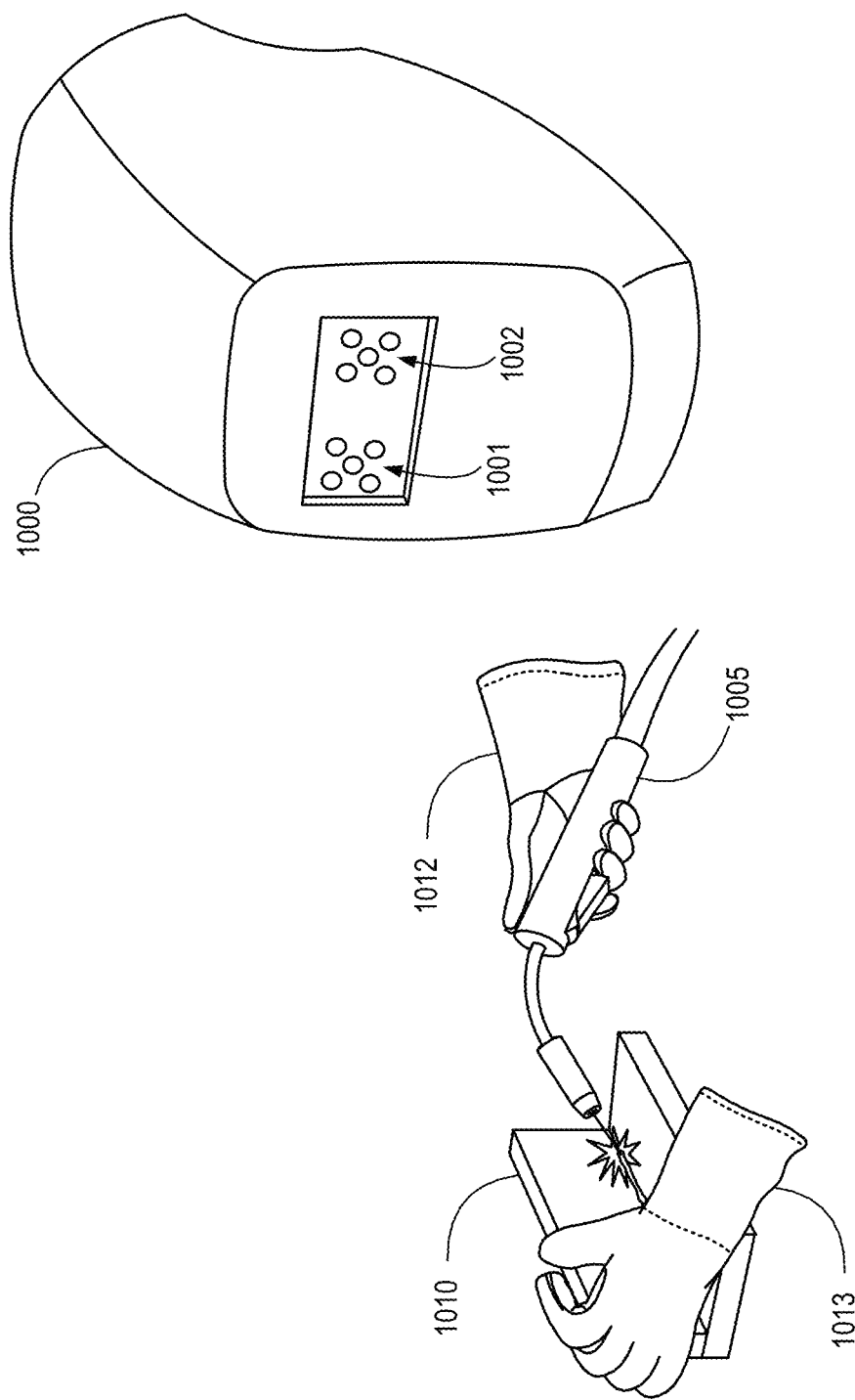
FIG. 10A illustrates an example of a welding mask with five cameras capturing images at different exposures and/or perspectives for each eye of the operator, according to one embodiment.

FIG. 10A illustrates an example of a welding mask 1000 with five cameras 1001 and 1002 capturing images at different exposures and/or perspectives for each eye of the operator, according to one embodiment. Each camera may capture a different perspective of the workpiece 1010, hands 1012 and 1013, and welder wand 1005. Each camera may also capture images at a different exposure level. The welder system may determine light field data for the scene (the workpiece 1010, hands 1012 and 1013, and welder wand 1005) based on the relative locations of the discrete cameras 1001 and 1002. The light field data may be used to directly generate HDR images.

Figure 10B:
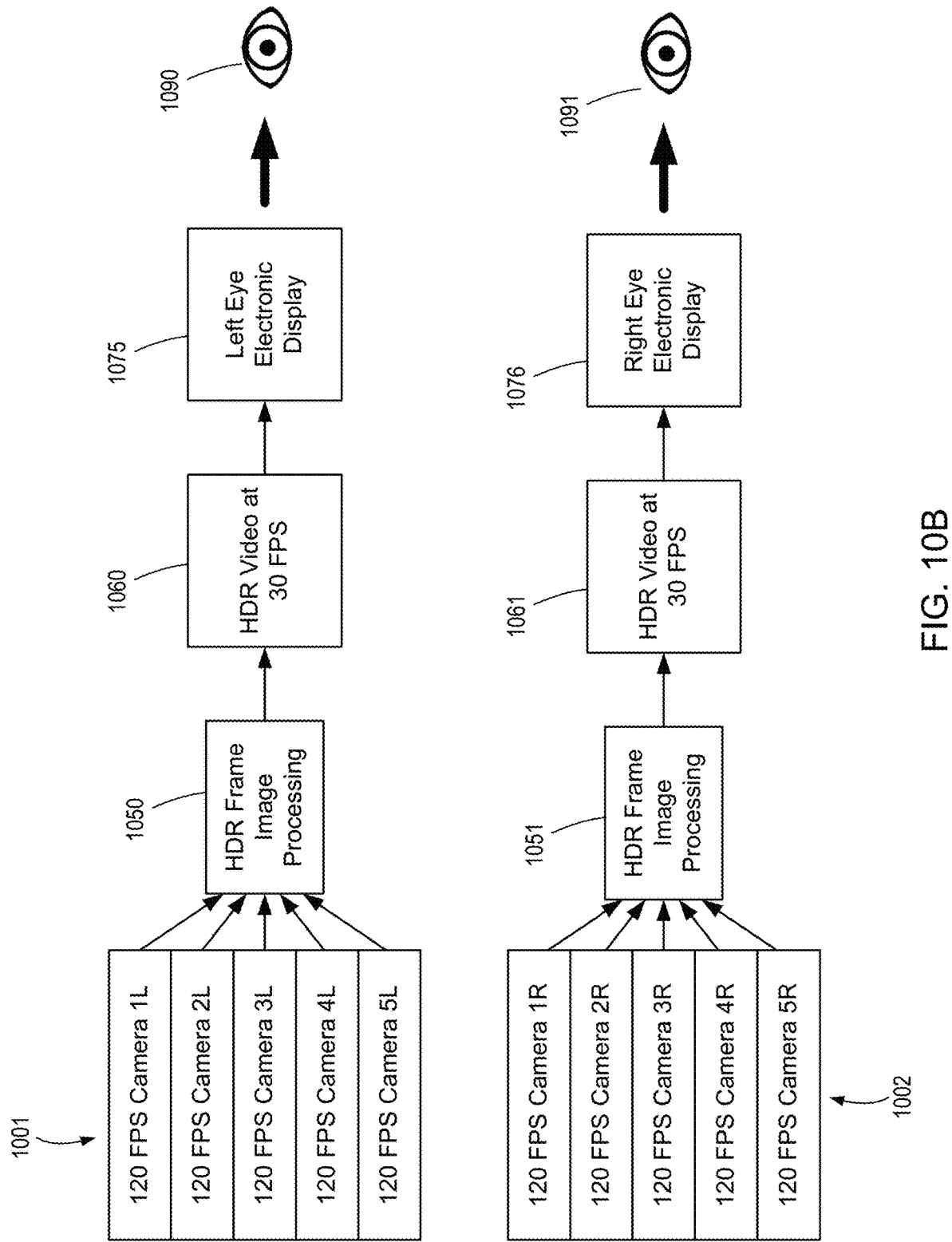
FIG. 10B illustrates a simplified block diagram of images from multiple cameras combined via HDR frame image processing to generate an HDR video for each eye of an operator, according to one embodiment.

FIG. 10B illustrates a simplified block diagram of images from multiple cameras combined via HDR frame image processing to generate an HDR video for each eye of an operator, according to one embodiment. As illustrated, five "left-eye" cameras 1001 capture images at 120 FPS to provide light field data to the system. An HDR frame image processing subsystem 1050 processes the light field data to generate an HDR frame. An HDR video 1060 is generated at 30 FPS that is fed to the left eye 1090 of the operator via a left eye electronic display 1075.

Similarly, five "right-eye" cameras 1002 capture images at 120 FPS to provide light field data to the system. An HDR frame image processing subsystem 1051 processes the light field data to generate an HDR frame. An HDR video 1061 is generated at 30 FPS that is fed to the right eye 1091 of the operator via a right eye electronic display 1076.

FIG. 11A illustrates an example of a welding mask 1100 with light field cameras 1101 and 1102 (e.g., plenoptic cameras) to directly capture light fields that can be used to generate HDR frames for HDR video feeds for each eye of an operator.

Figure 11B:
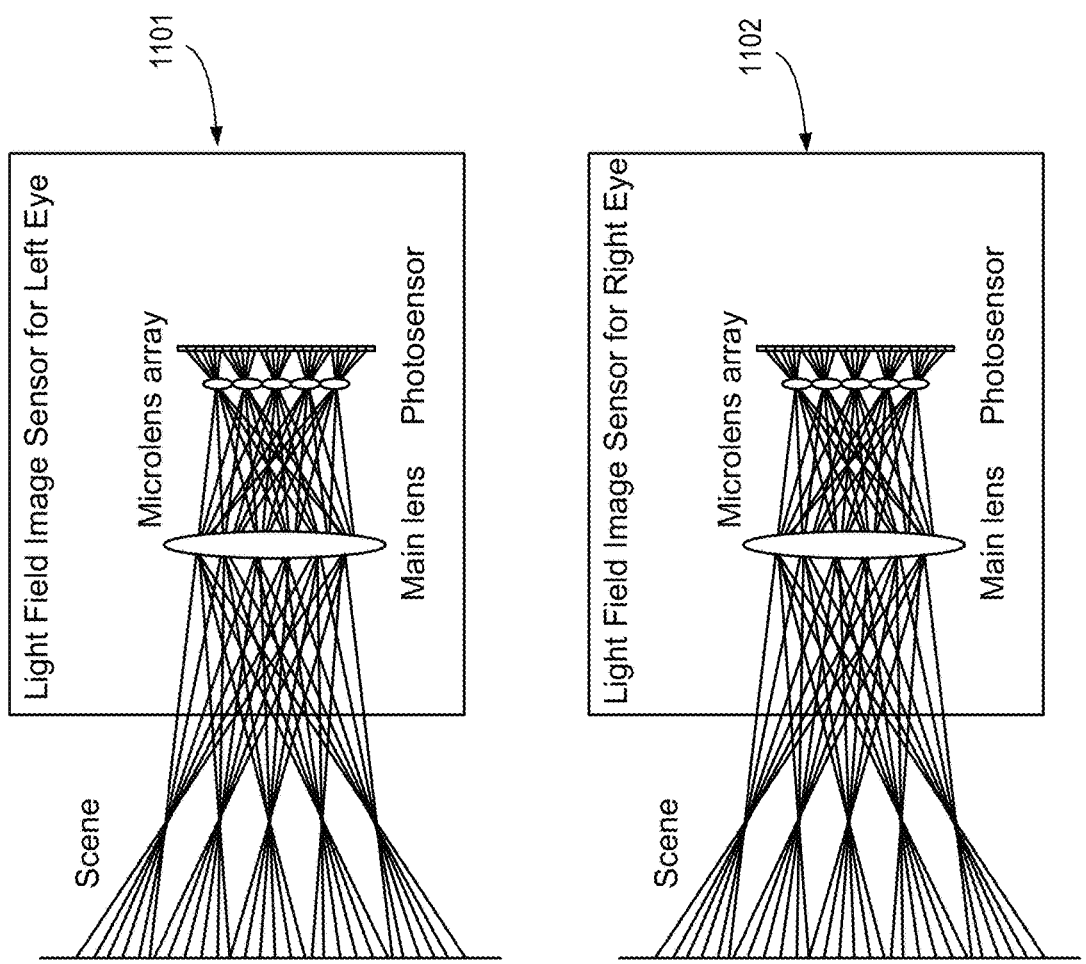
FIG. 11B illustrates a simplified block diagram of a light field camera, according to one embodiment.

FIG. 11B illustrates a simplified block diagram of light field cameras 1101 and 1102, according to one embodiment. As illustrated, each light field camera 1101 and 1102 may include a main lens, a microlens array, and a photosensor. Any of a wide variety of alternative plenoptic or other types of light field camera designs may be utilized.

Figure 11C:
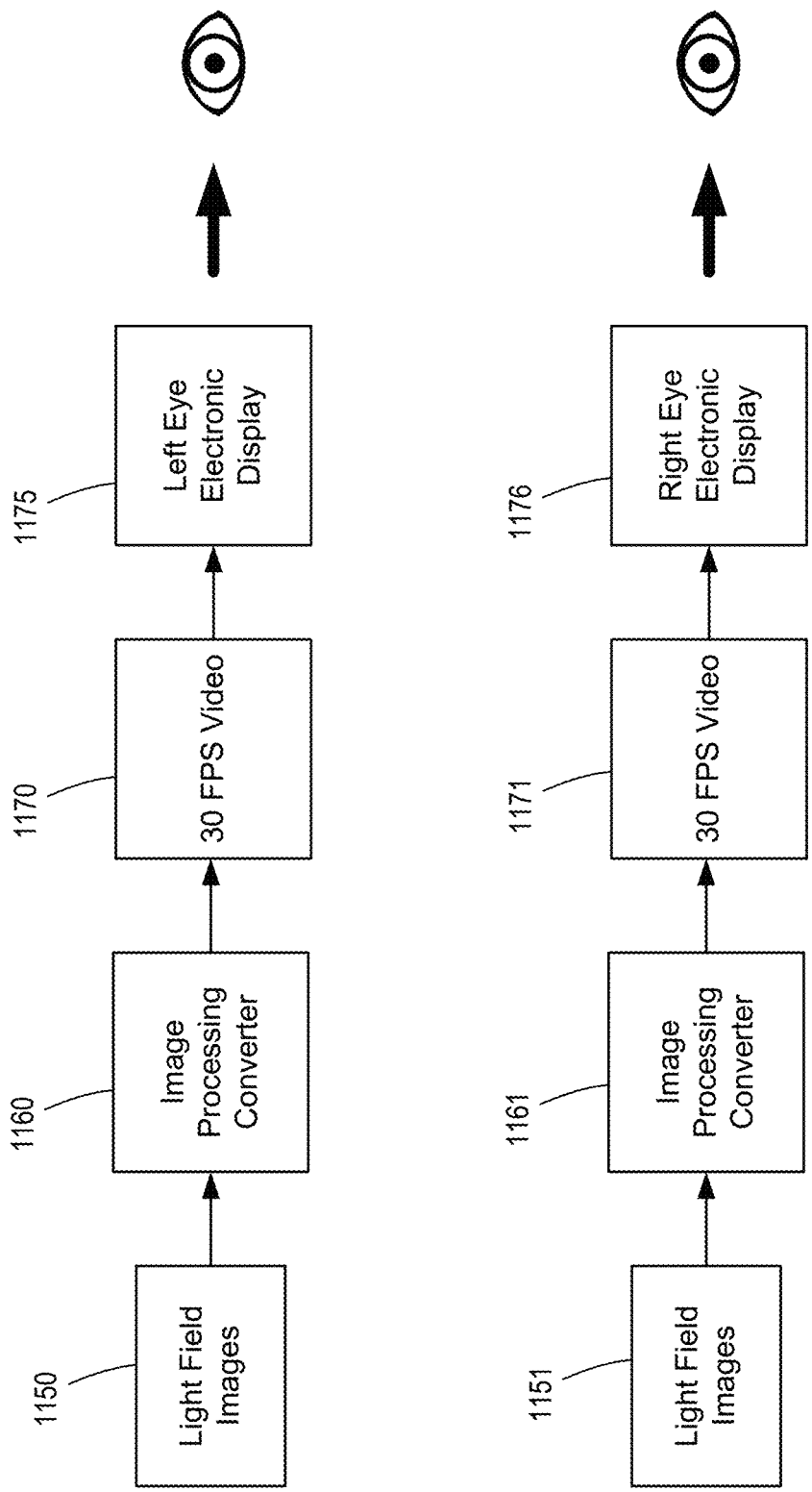
FIG. 11C illustrates a functional block diagram of a welding mask that utilizes light field images to generate a stereoscopic video feed for delivery to the eyes of an operator, according to one embodiment.

FIG. 11C illustrates a functional block diagram of a welding mask that utilizes light field images 1150 and 1151 to generate a stereoscopic video feed for delivery to the eyes of an operator, according to one embodiment. As illustrated, the light field images 1150 and 1151 are processed via an image processing converter 1160 and 1161 to generate HDR video at 30 FPS 1170 and 1171. The HDR video at 30 FPS 1170 and 1171 is displayed via left eye and right eye electronic displays 1175 and 1176.

The examples and illustrations provided relate to specific embodiments and implementations of a few of the many possible variations. It is understood that this disclosure is not limited to the precise configurations and components disclosed herein and that some embodiments may be combined and/or elements may be omitted from described embodiments. Accordingly, many changes may be made to the details of the above-described embodiments without departing from the underlying principles of this disclosure. The following claims are part of the present disclosure, are expressly incorporated into the detailed description, and are consistent with the various embodiments or combination of embodiments described herein. The scope of the present invention should, therefore, be determined in the context of and to at least encompass the claims below.

What is claimed is:

1. A welding mask, comprising:
a protective shell to provide physical protection to an operator of a welder;
a high-dynamic range (HDR) camera subsystem to:
receive data identifying an operational frequency of the welder;
select an exposure time as a submultiple of the identified operational frequency of the welder;
generate HDR frames of an HDR video using at least one image captured with the selected exposure time;
an image stabilization subsystem to compensate for movement of the welding mask during image capture;
an optical filter to attenuate at least some wavelengths of optical radiation; and
a digital electronic display positioned within the protective shell to display the HDR video to the operator.

2. A welding mask, comprising:
a protective shell to provide physical protection to an operator of a welder;
a high-dynamic range (HDR) camera subsystem to generate HDR frames of an HDR video;
an image stabilization subsystem to compensate for movement of the welding mask during image capture, wherein the image stabilization subsystem comprises an image sensor stabilization subsystem in which the image sensor physically moves relative to a lens element of the HDR camera subsystem;
an optical filter to attenuate at least some wavelengths of optical radiation; and
a digital electronic display positioned within the protective shell to display the HDR video to the operator.

3. The welding mask of claim 2, wherein the HDR camera subsystem comprises a bracketing imaging system to capture multiple images at different exposures that are combined to generate each HDR frame of the video.

4. The welding mask of claim 1, wherein the HDR camera subsystem is configured to generate a first HDR video for a right eye of the operator and a second HDR video for the left eye of the operator, and wherein the digital electronic display comprises a stereoscopic display to display the first HDR video to the right eye of the operator and the second HDR video to the left eye of the operator.

5. The welding mask of claim 2, wherein the camera subsystem is an asynchronous video capture system that captures frames of the video asynchronously with respect to an operating frequency of the welder.

6. The welding mask of claim 2, wherein each frame of the HDR video generated by the camera subsystem comprises at least one image captured with an exposure time that includes at least one half of a weld light intensity cycle of the welder.

7. The welding mask of claim 2, wherein each frame of the HDR video generated by the camera subsystem comprises at least one image captured with an exposure time that includes a single weld light intensity cycle of the welder.

8. The welding mask of claim 2, wherein each frame of the HDR video generated by the camera subsystem comprises at least one image captured with an exposure time that includes multiple weld light intensity cycles of the welder.

9. The welding mask of claim 2, wherein the HDR camera subsystem is configured to:
receive data identifying an operational frequency of the welder; and
select the exposure time of at least one image used to generate each HDR frame of the HDR video as a submultiple of the identified operational frequency of the welder.

10. The welding mask of claim 9, further comprising a weld cycle detection subsystem to:
detect a duration of each weld light intensity cycle of the welder, and
transmit data identifying the detected weld light intensity cycle duration to the HDR camera subsystem.

11. The welding mask of claim 9, further comprising a welder interface subsystem to:
receive data from the welder identifying the operational frequency, and
relay the data from the welder identifying the operational frequency to the HDR camera subsystem.

12. The welding mask of claim 2, wherein the HDR camera subsystem is configured to generate the HDR video with a frame rate that is a submultiple of the operational frequency of the welder.

13. The welding mask of claim 1, wherein the optical filter comprises an auto-darkening filter (ADF).

14. The welding mask of claim 1, wherein the image stabilization subsystem comprises an optical image stabilization lens system in which at least one lens element moves with respect to another lens element.

15. The welding mask of claim 2, wherein the HDR camera subsystem comprises an HDR light field imaging system to capture an HDR light field used to generate each HDR frame of the video.

16. The welding mask of claim 1, wherein the optical filter comprises a tunable auto-darkening filter, and
wherein the HDR camera subsystem tunes the tunable auto-darkening filter to selectively attenuate the optical radiation to achieve a target exposure of each frame of the video for the selected exposure time.

17. A welding mask, comprising:
a protective shell to provide physical protection to an operator of a welder;
a high dynamic range (HDR) camera subsystem with a plurality of cameras to:
receive data identifying an operational frequency of the welder;
select an exposure time for each camera that is a submultiple of the identified operational frequency of the welder; and
capture multiple images to generate HDR images as frames of videos from multiple perspectives at the selected exposure time for each respective camera;
wherein the HDR camera subsystem includes:
at least one auto-darkening filter (ADF) to attenuate at least some wavelengths of optical radiation generated during a welding process by the welder, and
an image stabilization subsystem to compensate for movement of the welding mask during image capture by each of the plurality of cameras, wherein the image stabilization subsystem comprises an image sensor stabilization subsystem in which the image sensor physically moves relative to a lens element of the HDR camera subsystem;

a video processing subsystem to generate a digitally rendered composite HDR video using the videos from the plurality of cameras; and a digital electronic display positioned within the protective shell to display the digitally rendered HDR composite video to the operator.

18. The welding mask of claim 17, wherein the HDR camera subsystem is configured to generate a first HDR video for a right eye of the operator and a second HDR video for the left eye of the operator, and wherein the digital electronic display comprises a stereoscopic display to display the first HDR video to the right eye of the operator and the second HDR video to the left eye of the operator.

* * * * *